US009469673B2

(12) United States Patent
Sheikh et al.

(10) Patent No.: US 9,469,673 B2
(45) Date of Patent: Oct. 18, 2016

(54) CRYSTALINE FORMS OF HCV INHIBITOR

(71) Applicant: AbbVie Inc., Waukegan, IL (US)

(72) Inventors: Ahmad Y. Sheikh, Deerfield, IL (US); Moiz Diwan, Gurnee, IL (US); Agnes E. Pal, Grayslake, IL (US); Yuchuan Gong, Waukegan, IL (US); Paul J. Brackemeyer, Mt. Prospect, IL (US); Geoff Zhang, Vernon Hills, IL (US); Seble Wagaw, Evanston, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/939,873

(22) Filed: Jul. 11, 2013

(65) Prior Publication Data

US 2014/0018518 A1 Jan. 16, 2014

Related U.S. Application Data

(60) Provisional application No. 61/670,905, filed on Jul. 12, 2012.

(51) Int. Cl.
*C07K 5/083* (2006.01)
*C07K 5/12* (2006.01)
*C07D 487/04* (2006.01)

(52) U.S. Cl.
CPC ............ *C07K 5/123* (2013.01); *C07D 487/04* (2013.01); *C07K 5/0804* (2013.01)

(58) Field of Classification Search
None
See application file for complete search history.

(56) References Cited

U.S. PATENT DOCUMENTS

| 7,314,516 | B2* | 1/2008 | Kozyuk et al. | 117/68 |
| 8,642,538 | B2 | 2/2014 | Ku et al. | |
| 2010/0144608 | A1 | 6/2010 | Ku et al. | |
| 2011/0312973 | A1 | 12/2011 | Liepold et al. | |
| 2012/0213827 | A1* | 8/2012 | Chatterji et al. | 424/400 |
| 2014/0148573 | A1 | 5/2014 | Ku et al. | |
| 2015/0175612 | A1 | 6/2015 | Brackemeyer et al. | |

FOREIGN PATENT DOCUMENTS

WO  WO-2010-083894 A1  7/2010

OTHER PUBLICATIONS

Day G.M., et al., "Significant Progress in Predicting the Crystal Structures of Small Organic Molecules—a Report on the Fourth Blind Test," Acta Crystallographica.Section B, 2009, vol. 65 (Pt 2), pp. 107-125.
Fiedler., "Encyclopedia of Excipients for Pharmaceuticals, Cosmetics and related Areas," 5th Edition, Hoepfner E. M., et al., eds., Editio Cantor Verlag Aulendorf, 2002, Table of Contents.
International Search Report and Written Opinion for Application No. PCT/US2013/050023, mailed on Sep. 25, 2013, 8 pages.
Masters K., "Spray Drying Handbook" 4th Edition, John Wiley & Sons, 1985, Table of Contents.

* cited by examiner

*Primary Examiner* — Christina Bradley
(74) *Attorney, Agent, or Firm* — Dana M. Gordon; Foley Hoag LLP

(57) ABSTRACT

The present invention features crystalline forms of Compound I. In one embodiment, a crystalline form of Compound I has characteristic peaks in the PXRD pattern at values of two theta (° 2θ) of 10.7, 11.6, 12.7, 13.0, 13.2, 13.7, 14.5, 18.7, 19.0, and 19.9 after equilibration at 43% relative humidity.

12 Claims, 8 Drawing Sheets

CRYSTALINE FORMS OF HCV INHIBITOR

This application claims priority from U.S. Provisional Application No. 61/670,905, filed Jul. 12, 2012, the entire content of which is incorporated herein by reference.

FIELD OF THE INVENTION

The present invention relates to crystalline polymorphs of Compound I, compositions comprising the same, and methods of using the same to prepare pharmaceutical compositions.

BACKGROUND

The hepatitis C virus (HCV) is an RNA virus belonging to the *Hepacivirus* genus in the Flaviviridae family. The enveloped HCV virion contains a positive stranded RNA genome encoding all known virus-specific proteins in a single, uninterrupted, open reading frame. The open reading frame comprises approximately 9500 nucleotides and encodes a single large polyprotein of about 3000 amino acids. The polyprotein comprises a core protein, envelope proteins E1 and E2, a membrane bound protein p7, and the non-structural proteins NS2, NS3, NS4A, NS4B, NS5A and NS5B.

HCV infection is associated with progressive liver pathology, including cirrhosis and hepatocellular carcinoma. Chronic hepatitis C may be treated with peginterferon-alpha in combination with ribavirin. Substantial limitations to efficacy and tolerability remain as many users suffer from side effects, and viral elimination from the body is often inadequate. Therefore, there is a need for new drugs to treat HCV infection.

SUMMARY OF THE INVENTION

The present invention features Form A, B, C, D, E, F, F, G and H, as well as Class 2, of the crystalline form of Compound I.

In one aspect, the present invention features a crystalline form of Compound I, wherein, upon equilibrated at 43% relative humidity, said crystalline form has characteristic peaks in PXRD pattern at values of two theta (° 2θ) of 10.7, 11.6, 12.7, 13.0, 13.2, 13.7, 14.5, 18.7, 19.0, and 19.9.

In one embodiment of this aspect, upon equilibrated at 43% relative humidity, the crystalline form has characteristic peaks in PXRD pattern at values of two theta (° 2θ) of 10.70, 11.57, 12.75, 13.02, 13.18, 13.66, 14.47, 18.66, 18.96, and 19.94.

In another embodiment of this aspect, upon equilibrated at 43% relative humidity, the crystalline form has characteristic peaks in PXRD pattern at values of two theta (° 2θ) of 10.5, 10.7, 11.6, 12.7, 13.0, 13.2, 13.7, 14.5, 17.3, 18.7, 19.0, 19.9, 21.9, 23.3, 24.3, 25.2, 25.6, 26.6, 27.2, and 30.0.

In yet another embodiment of this aspect, upon equilibrated at 43% relative humidity, the crystalline form has characteristic peaks in PXRD pattern at values of two theta (° 2θ) of 10.54, 10.70, 11.57, 12.75, 13.02, 13.18, 13.66, 14.47, 17.35, 18.66, 18.96, 19.94, 21.90, 23.31, 24.34, 25.19, 25.56, 26.64, 27.24, and 29.95.

In still another embodiment, upon equilibrated at 43% relative humidity, the crystalline form has characteristic peaks in PXRD pattern at values of two theta (° 2θ) of 5.8, 10.5, 10.7, 11.6, 12.7, 13.0, 13.2, 13.7, 14.5, 14.9, 17.3, 17.9, 18.7, 19.0, 19.7, 19.9, 20.5, 20.9, 21.4, 21.9, 22.4, 23.0, 23.3, 23.8, 24.3, 25.2, 25.6, 26.6, 27.2, and 30.0.

In still yet another embodiment, upon equilibrated at 43% relative humidity, the crystalline form has characteristic peaks in PXRD pattern at values of two theta (° 2θ) of 5.80, 10.54, 10.70, 11.57, 12.75, 13.02, 13.18, 13.66, 14.47, 14.88, 17.35, 17.92, 18.66, 18.96, 19.69, 19.94, 20.45, 20.86, 21.42, 21.90, 22.41, 22.98, 23.31, 23.84, 24.34, 25.19, 25.56, 26.64, 27.24, and 29.95.

In yet another embodiment, upon equilibrated at 43% relative humidity, the crystalline form has characteristic PXRD peaks as shown in FIG. 7.

In another aspect, the present invention features compositions comprising a crystalline form of the invention (e.g., Form A, B, C, D, E, F, F, G or H, or Class 2, of the crystalline form of Compound I).

In still another aspect, the present invention features processes of making a composition comprising Compound I (or a pharmaceutically acceptable salt thereof). The processes comprise dissolving a crystalline form of the invention (e.g., Form A, B, C, D, E, F, F, G or H, or Class 2, of the crystalline form of Compound I) in a solvent. In one embodiment, the solvent is a molten hydrophilic polymer, such as molten copovidone. In another embodiment, the solvent is a hydrophilic polymer such as copovidone, and the crystalline form of Compound I is dissolved in the polymer using a melt extrusion process.

In yet another aspect, the present invention features processes for making a crystalline form of the invention (e.g., Form A, B, C, D, E, F, F, G or H, or Class 2, of the crystalline form of Compound I). The processes comprise adding seeds of a crystalline form of the invention (e.g., Form A, B, C, D, E, F, F, G or H, or Class 2) to a solution comprising Compound I. Preferably, the seeds are generated from a solution of Compound I (e.g., a supersaturated solution of Compound I) using a homogenization device (e.g., a rotor-stator) and in the presence of seed crystals of a crystalline form of the invention (e.g., Form A, B, C, D, E, F, F, G or H, or Class 2). Wet-milling technique may also be used to generate the seeds.

Other features, objects, and advantages of the present invention are apparent in the detailed description that follows. It should be understood, however, that the detailed description, while indicating preferred embodiments of the invention, are given by way of illustration only, not limitation. Various changes and modifications within the scope of the invention will become apparent to those skilled in the art from the detailed description

DESCRIPTION OF THE DRAWINGS

The drawings are provided for illustration, not limitation.

DETAILED DESCRIPTION

Figure 1:
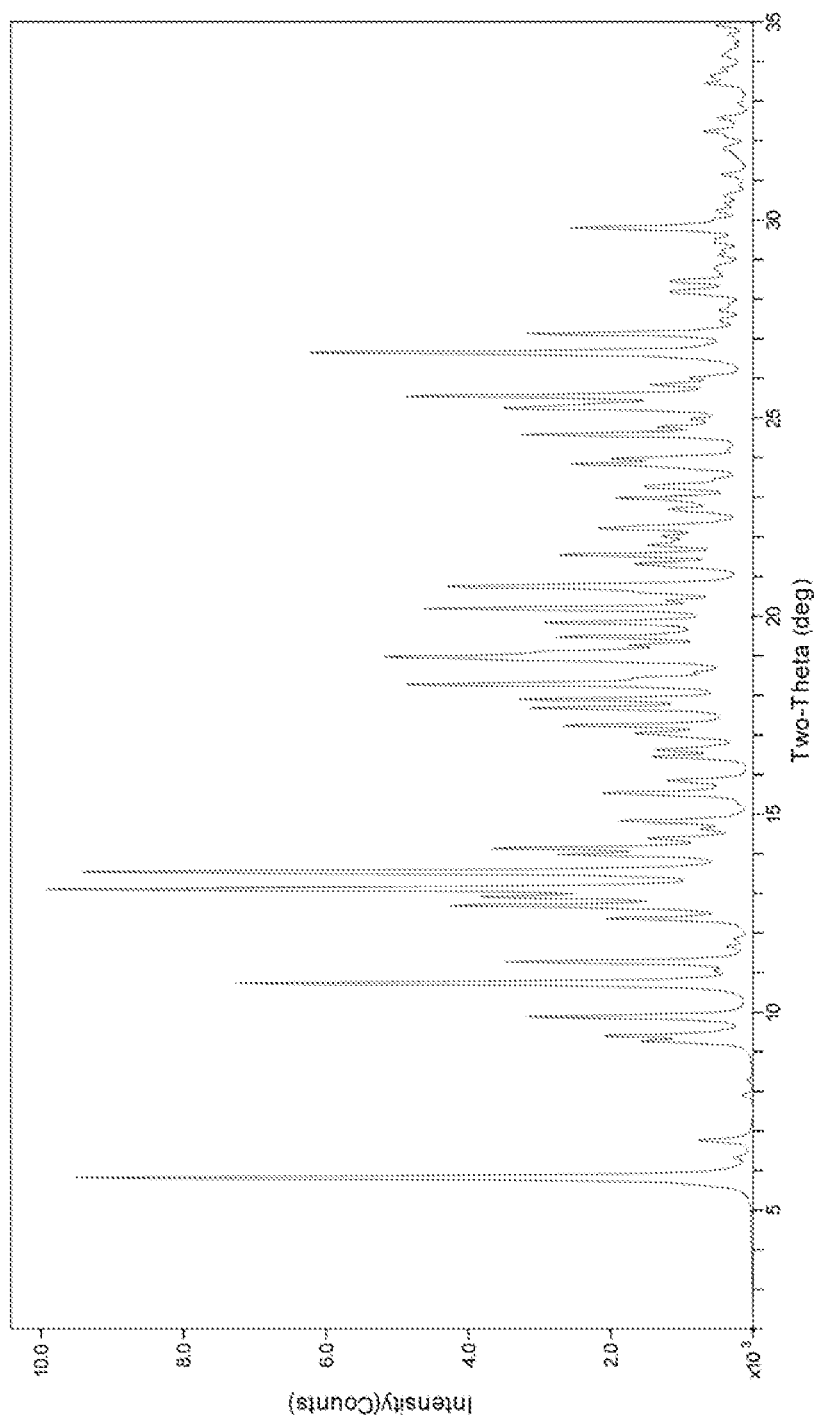
FIG. 1 shows the calculated powder X-ray diffraction (PXRD) pattern of Form A of Compound I; the calculation is based on the resolved crystal structure.

The present invention features crystalline polymorphs of (2R,6S,13aS,14aR,16aS,Z)-N-(cyclopropylsulfonyl)-6-(5-methylpyrazine-2-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide

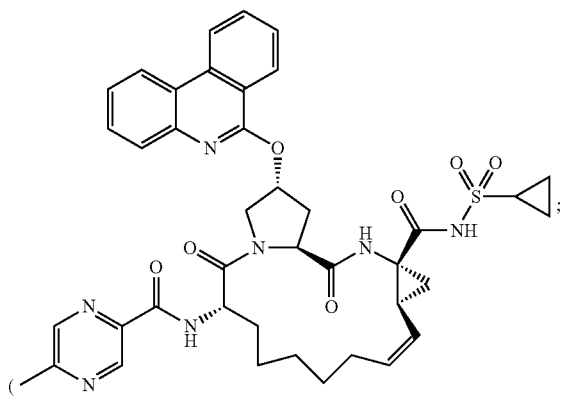 [SMILES: Cc1cnc(C(=O)N[C@H]2CCCCC/C=C\[C@@H]3C[C@@]3(C(=O)NS(=O)(=O)C3CC3)NC(=O)[C@@H]3C[C@@H](Oc4nc5ccccc5c5ccccc45)CN3C2=O)cn1]

herein "Compound I"). Compound I is a potent HCV protease inhibitor. The synthesis and formulation of Compound I are described in U.S. Patent Application Publication Nos. 2010/0144608 and 2011/0312973, both of which are incorporated herein by reference in their entireties.

Crystal structures of large molecules such as Compound I are generally not predictable. Several novel crystalline polymorphs of Compound I were isolated according to the present invention and, the existence of these polymorphs had not been either predicted or expected prior to their isolation. It was also surprisingly found that, as compared to the crystalline hydrate described in Example 49d of U.S. Patent Application Publication No. 2010/0144608, these novel polymorphs can have improved processability and yield and can be more easily purified due to their relatively large particle sizes. Lack of significant amounts of organic solvents also make these polymorphs especially suitable for use in melt extrusion processes to make pharmaceutical compositions that comprise Compound I.

In one aspect, the invention features a crystalline form of Compound I (hereinafter Form A), which has characteristic peaks in the powder X-ray diffraction (PXRD) pattern at values of two theta (° 2θ) of 5.8, 10.7, 11.1, 11.8, 13.1, 13.5, 18.3, 20.2, 25.5, and 26.7. Preferably, these peaks have higher intensities than other peaks in the PXRD pattern. Also preferably, these peaks have relative intensities of 92%, 70%, 84%, 90%, 100%, 88%, 44%, 40%, 49%, and 57%, respectively.

In one embodiment of this aspect of the invention, Form A has characteristic peaks in the PXRD pattern at values of two theta (° 2θ) of 5.82, 10.73, 11.05, 11.84, 13.11, 13.54, 18.29, 20.19, 25.55, and 26.66. Preferably, these peaks have higher intensities than other peaks in the PXRD pattern. Also preferably, these peaks have relative intensities of 92%, 70%, 84%, 90%, 100%, 88%, 44%, 40%, 49%, and 57%, respectively.

In another embodiment of this aspect of the invention, Form A has characteristic peaks in the PXRD pattern at values of two theta (° 2θ) of 5.8, 9.9, 10.7, 11.1, 11.3, 11.8, 12.7, 12.9, 13.1, 13.5, 14.1, 17.9, 18.3, 19.0, 20.2, 20.7, 24.6, 25.3, 25.5, and 26.7. Preferably, these peaks have higher intensities than other peaks in the PXRD pattern. Also preferably, these peaks have relative intensities of 92%, 30%, 70%, 84%, 33%, 90%, 38%, 33%, 100%, 88%, 33%, 29%, 44%, 29%, 40%, 37%, 31%, 34%, 49%, and 57%, respectively.

In yet another embodiment of this aspect of the invention, Form A has characteristic peaks in the PXRD pattern at values of two theta (° 2θ) of 5.82, 9.89, 10.73, 11.05, 11.27, 11.84, 12.69, 12.93, 13.11, 13.54, 14.14, 17.90, 18.29, 18.97, 20.19, 20.75, 24.58, 25.26, 25.55, and 26.66. Preferably, these peaks have higher intensities than other peaks in the PXRD pattern. Also preferably, these peaks have relative intensities of 92%, 30%, 70%, 84%, 33%, 90%, 38%, 33%, 100%, 88%, 33%, 29%, 44%, 29%, 40%, 37%, 31%, 34%, 49%, and 57%, respectively.

In still another embodiment of this aspect of the invention, Form A has characteristic peaks in the PXRD pattern at values of two theta (° 2θ) of 5.8, 6.8, 9.3, 9.4, 9.9, 10.7, 11.1, 11.3, 11.8, 12.4, 12.7, 12.9, 13.1, 13.5, 14.0, 14.1, 14.4, 14.8, 15.5, 15.9, 16.5, 16.6, 17.0, 17.2, 17.7, 17.9, 18.3, 19.0, 19.3, 19.5, 19.8, 20.2, 20.7, 21.3, 21.5, 21.8, 22.0, 22.2, 22.7, 23.0, 23.3, 23.8, 24.0, 24.6, 24.8, 25.0, 25.3, 25.5, 25.8, 26.7, 27.1, and 29.8. Preferably, these peaks have higher intensities than other peaks in the PXRD pattern. Also preferably, these peaks have relative intensities of 92%, 7%, 15%, 21%, 30%, 70%, 84%, 33%, 90%, 19%, 38%, 33%, 100%, 88%, 23%, 33%, 12%, 17%, 18%, 11%, 13%, 12%, 9%, 23%, 28%, 29%, 44%, 29%, 9%, 20%, 23%, 40%, 37%, 10%, 22%, 9%, 7%, 17%, 8%, 16%, 12%, 18%, 17%, 31%, 10%, 5%, 34%, 49%, 11%, 57%, 28%, and 25%, respectively.

In still another embodiment of this aspect of the invention, Form A has characteristic peaks in the PXRD pattern at values of two theta (° 2θ) of 5.82, 6.77, 9.27, 9.40, 9.89, 10.73, 11.05, 11.27, 11.84, 12.37, 12.69, 12.93, 13.11, 13.54, 13.98, 14.14, 14.39, 14.82, 15.53, 15.85, 16.46, 16.63, 17.04, 17.24, 17.68, 17.90, 18.29, 18.97, 19.26, 19.48, 19.84, 20.19, 20.75, 21.32, 21.54, 21.80, 22.02, 22.23, 22.70, 22.98, 23.26, 23.84, 23.97, 24.58, 24.77, 24.98, 25.26, 25.55, 25.85, 26.66, 27.14, and 29.81. Preferably, these peaks have higher intensities than other peaks in the PXRD pattern. Also preferably, these peaks have relative intensities of 92%, 7%, 15%, 21%, 30%, 70%, 84%, 33%, 90%, 19%, 38%, 33%, 100%, 88%, 23%, 33%, 12%, 17%, 18%, 11%, 13%, 12%, 9%, 23%, 28%, 29%, 44%, 29%, 9%, 20%, 23%, 40%, 37%, 10%, 22%, 9%, 7%, 17%, 8%, 16%, 12%, 18%, 17%, 31%, 10%, 5%, 34%, 49%, 11%, 57%, 28%, and 25%, respectively.

In still another embodiment of this aspect of the invention, Form A has characteristic PXRD peaks as shown in FIG. 1.

In still another embodiment of this aspect of the invention, Form A has a crystalline structure as defined in Table 1.

TABLE 1

| Crystal Structure of Form A | |
|---|---|
| Crystal Form | Form A |
| Lattice Type | Triclinic |
| Space Group | P1 |
| a (Å) | 15 |
| b (Å) | 16 |
| c (Å) | 18 |

TABLE 1-continued

Crystal Structure of Form A

| Crystal Form | Form A |
| --- | --- |
| α (°) | 108 |
| β (°) | 110 |
| γ (°) | 92 |
| Volume (Å$^3$) | 3800 |
| Z | 4 |

Without limiting this aspect of the invention to any particular theory or calculation, Form A typically contains about 0 molecule of water per molecule of Compound I.

In another aspect, the invention features another crystalline form of Compound I (hereinafter Form B), which has characteristic peaks in the PXRD pattern at values of two theta (° 2θ) of 11.6, 13.1, 13.4, 14.3, 14.7, 19.2, 22.3, 24.1, 25.3, and 27.8. Preferably, these peaks have higher intensities than other peaks in the PXRD pattern. Also preferably, these peaks have relative intensities of 39%, 100%, 88%, 49%, 41%, 34%, 30%, 36%, 34%, and 50%, respectively.

In one embodiment of this aspect of the invention, Form B has characteristic peaks in the PXRD pattern at values of two theta (° 2θ) of 11.62, 13.06, 13.35, 14.31, 14.67, 19.17, 22.34, 24.08, 25.35, and 27.85. Preferably, these peaks have higher intensities than other peaks in the PXRD pattern. Also preferably, these peaks have relative intensities of 39%, 100%, 88%, 49%, 41%, 34%, 30%, 36%, 34%, and 50%, respectively.

In another embodiment of this aspect of the invention, Form B has characteristic peaks in the PXRD pattern at values of two theta (° 2θ) of 10.7, 10.9, 11.6, 13.1, 13.4, 13.8, 14.3, 14.7, 17.5, 17.6, 19.2, 20.0, 22.3, 24.1, 24.5, 25.3, 26.3, 27.8, 28.1, and 31.3. Preferably, these peaks have higher intensities than other peaks in the PXRD pattern. Also preferably, these peaks have relative intensities of 23%, 22%, 39%, 100%, 88%, 23%, 49%, 41%, 27%, 22%, 34%, 20%, 30%, 36%, 21%, 34%, 20%, 50%, 20%, and 23%, respectively.

In another embodiment of this aspect of the invention, Form B has characteristic peaks in the PXRD pattern at values of two theta (° 2θ) of 10.69, 10.88, 11.62, 13.06, 13.35, 13.79, 14.31, 14.67, 17.47, 17.62, 19.17, 19.97, 22.34, 24.08, 24.51, 25.35, 26.27, 27.85, 28.15, and 31.29. Preferably, these peaks have higher intensities than other peaks in the PXRD pattern. Also preferably, these peaks have relative intensities of 23%, 22%, 39%, 100%, 88%, 23%, 49%, 41%, 27%, 22%, 34%, 20%, 30%, 36%, 21%, 34%, 20%, 50%, 20%, and 23%, respectively.

In another embodiment of this aspect of the invention, Form B has characteristic peaks in the PXRD pattern at values of two theta (° 2θ) of 10.7, 10.9, 11.6, 13.1, 13.4, 13.8, 14.3, 14.7, 15.4, 17.5, 17.6, 18.2, 19.2, 19.5, 20.0, 20.3, 20.5, 20.9, 21.7, 21.9, 22.3, 22.6, 23.3, 24.1, 24.3, 24.5, 25.3, 25.7, 25.9, 26.3, 27.4, 27.5, 27.8, 28.1, and 31.3. Preferably, these peaks have higher intensities than other peaks in the PXRD pattern. Also preferably, these peaks have relative intensities of 23%, 22%, 39%, 100%, 88%, 23%, 49%, 41%, 6%, 27%, 22%, 7%, 34%, 14%, 20%, 9%, 19%, 9%, 8%, 13%, 30%, 10%, 14%, 36%, 16%, 21%, 34%, 19%, 6%, 20%, 8%, 6%, 50%, 20%, and 23%, respectively.

In another embodiment of this aspect of the invention, Form B has characteristic peaks in the PXRD pattern at values of two theta (° 2θ) of 10.69, 10.88, 11.62, 13.06, 13.35, 13.79, 14.31, 14.67, 15.39, 17.47, 17.62, 18.18, 19.17, 19.47, 19.97, 20.29, 20.51, 20.87, 21.69, 21.86, 22.34, 22.64, 23.26, 24.08, 24.25, 24.51, 25.35, 25.66, 25.89, 26.27, 27.35, 27.55, 27.85, 28.15, and 31.29. Preferably, these peaks have higher intensities than other peaks in the PXRD pattern. Also preferably, these peaks have relative intensities of 23%, 22%, 39%, 100%, 88%, 23%, 49%, 41%, 6%, 27%, 22%, 7%, 34%, 14%, 20%, 9%, 19%, 9%, 8%, 13%, 30%, 10%, 14%, 36%, 16%, 21%, 34%, 19%, 6%, 20%, 8%, 6%, 50%, 20%, and 23%, respectively.

Figure 2:
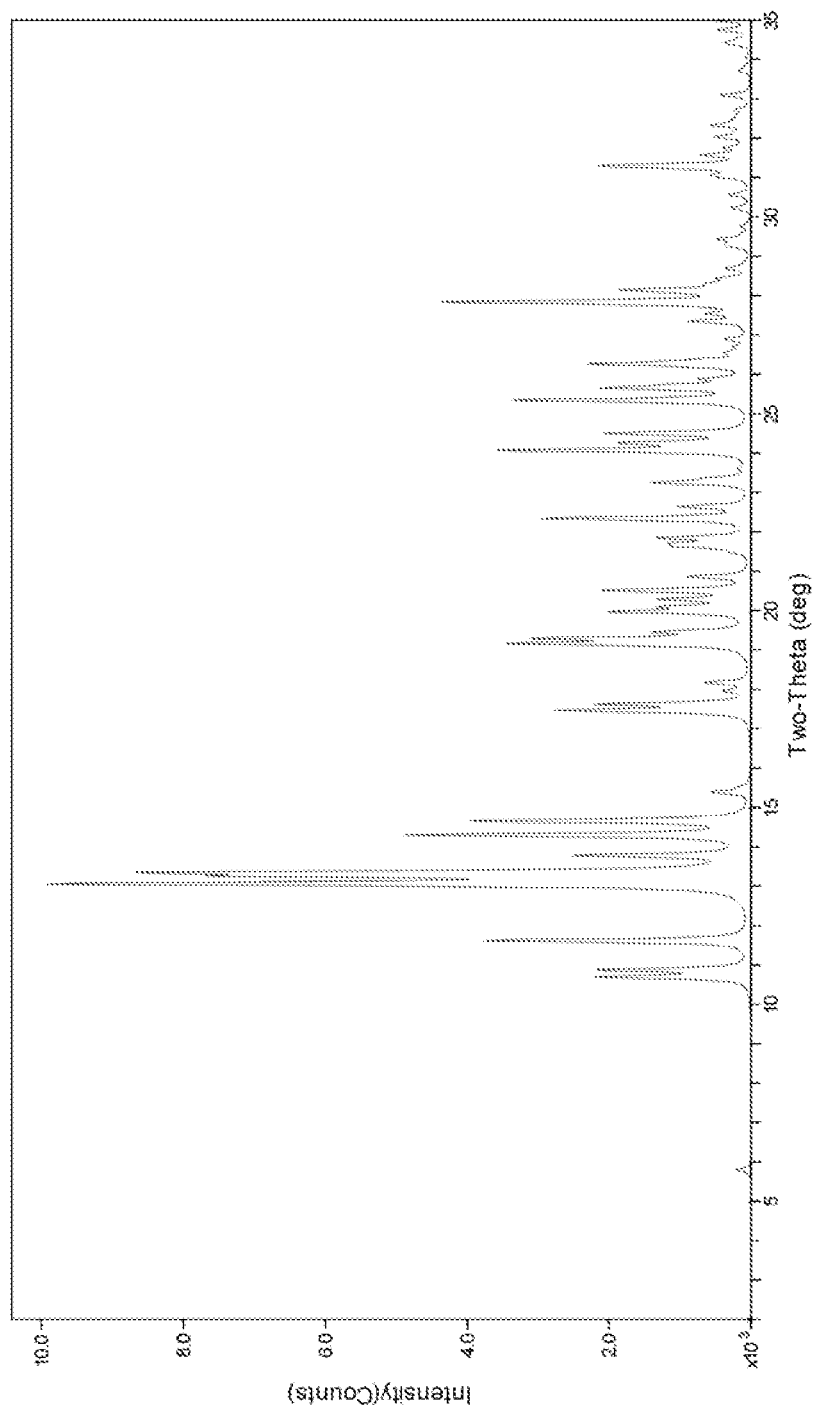
FIG. 2 depicts the calculated PXRD pattern of Form B of Compound I; the calculation is based on the resolved crystal structure.

In still another embodiment of this aspect of the invention, Form B has characteristic PXRD peaks as shown in FIG. 2.

In still another embodiment of this aspect of the invention, Form B has a crystalline structure as defined in Table 2.

TABLE 2

Crystal Structure of Form B

| Crystal Form | Form B |
| --- | --- |
| Lattice Type | Trilinic |
| Space Group | P1 |
| a (Å) | 7 |
| b (Å) | 9 |
| c (Å) | 16 |
| α (°) | 100 |
| β (°) | 99 |
| γ (°) | 111 |
| Volume (Å$^3$) | 963 |
| Z | 1 |

Without limiting this aspect of the invention to any particular theory or calculation, Form B typically contains about 2 molecules of water per molecule of Compound I.

In yet another aspect, the invention features another crystalline form of Compound I (hereinafter Form C), which has characteristic peaks in the PXRD pattern at values of two theta (° 2θ) of 11.6, 12.9, 13.1, 13.3, 14.2, 14.5, 19.1, 23.8, 25.1, and 27.7. Preferably, these peaks have higher intensities than other peaks in the PXRD pattern. Also preferably, these peaks have relative intensities of 38%, 100%, 53%, 68%, 43%, 37%, 33%, 38%, 36%, and 51%, respectively.

In one embodiment of this aspect of the invention, Form C has characteristic peaks in the PXRD pattern at values of two theta (° 2θ) of 11.58, 12.94, 13.14, 13.34, 14.22, 14.52, 19.06, 23.84, 25.14, and 27.66. Preferably, these peaks have higher intensities than other peaks in the PXRD pattern. Also preferably, these peaks have relative intensities of 38%, 100%, 53%, 68%, 43%, 37%, 33%, 38%, 36%, and 51%, respectively.

In another embodiment of this aspect of the invention, Form C has characteristic peaks in the PXRD pattern at values of two theta (° 2θ) of 10.8, 11.6, 12.9, 13.1, 13.3, 13.7, 14.2, 14.5, 17.4, 19.1, 19.2, 19.9, 20.4, 22.2, 23.8, 24.5, 25.1, 25.4, 26.0, and 27.7. Preferably, these peaks have higher intensities than other peaks in the PXRD pattern. Also preferably, these peaks have relative intensities of 25%, 38%, 100%, 53%, 68%, 24%, 43%, 37%, 27%, 33%, 28%, 22%, 25%, 25%, 38%, 21%, 36%, 23%, 25%, and 51%, respectively.

In another embodiment of this aspect of the invention, Form C has characteristic peaks in the PXRD pattern at values of two theta (° 2θ) of 10.84, 11.58, 12.94, 13.14, 13.34, 13.70, 14.22, 14.52, 17.40, 19.06, 19.18, 19.86, 20.40, 22.18, 23.84, 24.46, 25.14, 25.42, 26.04, and 27.66. Preferably, these peaks have higher intensities than other peaks in the PXRD pattern. Also preferably, these peaks have relative intensities of 25%, 38%, 100%, 53%, 68%, 24%, 43%, 37%, 27%, 33%, 28%, 22%, 25%, 25%, 38%, 21%, 36%, 23%, 25%, and 51%, respectively.

In another embodiment of this aspect of the invention, Form C has characteristic peaks in the PXRD pattern at values of two theta (° 2θ) of 10.7, 10.8, 11.6, 12.9, 13.1, 13.3, 13.7, 14.2, 14.5, 15.3, 17.4, 17.6, 18.1, 19.1, 19.2, 19.3, 19.9, 20.2, 20.4, 20.8, 21.6, 21.8, 22.2, 22.6, 23.1, 23.3, 23.8, 24.1, 24.5, 25.1, 25.4, 25.8, 26.0, 27.1, 27.3, 27.7, 27.9, and 31.1. Preferably, these peaks have higher intensities than other peaks in the PXRD pattern. Also preferably, these peaks have relative intensities of 19%, 25%, 38%, 100%, 53%, 68%, 24%, 43%, 37%, 7%, 27%, 18%, 6%, 33%, 28%, 12%, 22%, 11%, 25%, 9%, 10%, 16%, 25%, 10%, 16%, 6%, 38%, 16%, 21%, 36%, 23%, 5%, 25%, 11%, 8%, 51%, 17%, and 18%, respectively.

In another embodiment of this aspect of the invention, Form C has characteristic peaks in the PXRD pattern at values of two theta (° 2θ) of 10.68, 10.84, 11.58, 12.94, 13.14, 13.34, 13.70, 14.22, 14.52, 15.28, 17.40, 17.62, 18.06, 19.06, 19.18, 19.32, 19.86, 20.20, 20.40, 20.80, 21.58, 21.76, 22.18, 22.62, 23.12, 23.26, 23.84, 24.14, 24.46, 25.14, 25.42, 25.78, 26.04, 27.14, 27.26, 27.66, 27.92, and 31.12. Preferably, these peaks have higher intensities than other peaks in the PXRD pattern. Also preferably, these peaks have relative intensities of 19%, 25%, 38%, 100%, 53%, 68%, 24%, 43%, 37%, 7%, 27%, 18%, 6%, 33%, 28%, 12%, 22%, 11%, 25%, 9%, 10%, 16%, 25%, 10%, 16%, 6%, 38%, 16%, 21%, 36%, 23%, 5%, 25%, 11%, 8%, 51%, 17%, and 18%, respectively.

Figure 3:
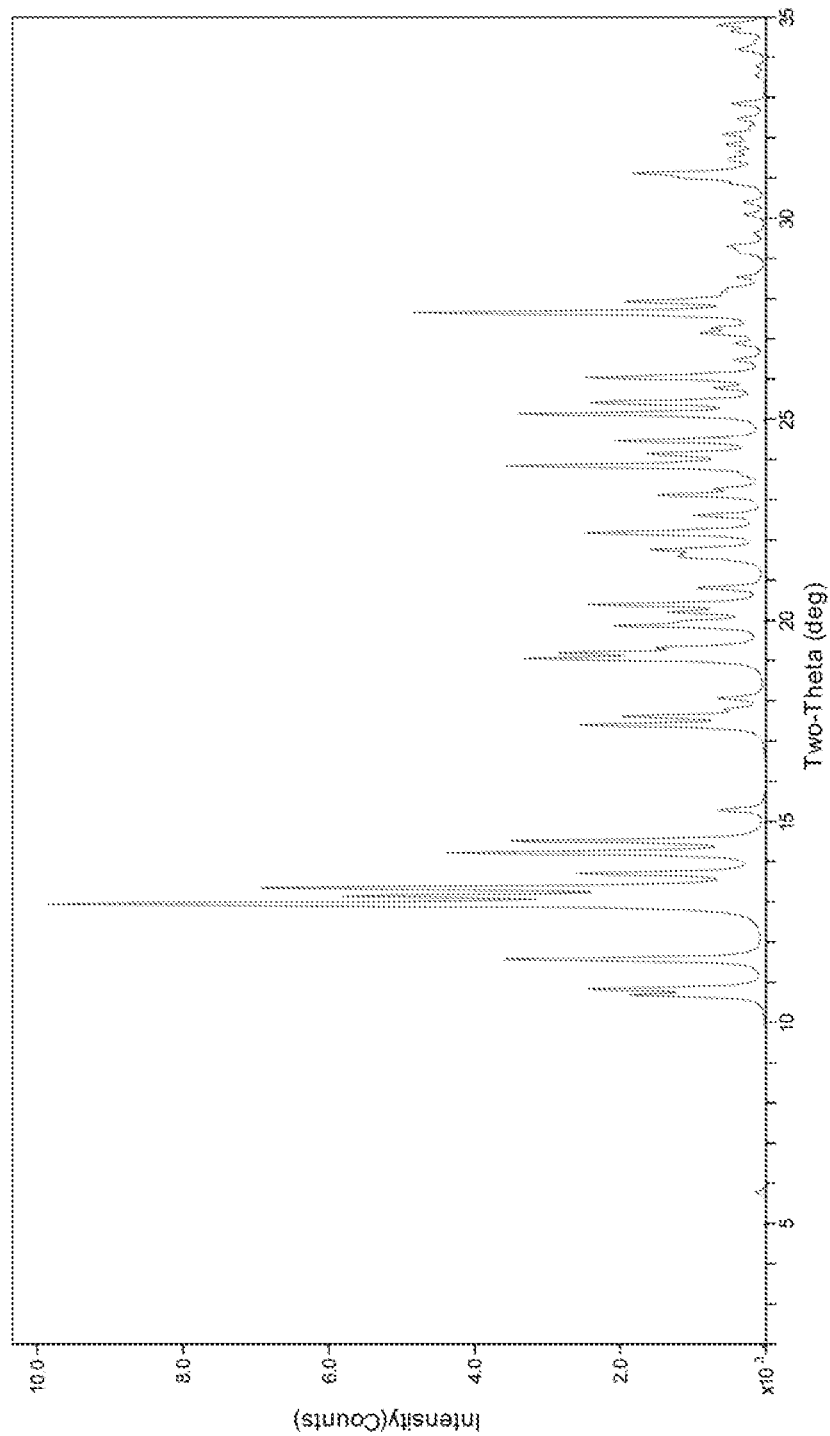
FIG. 3 illustrates the calculated PXRD pattern of Form C of Compound I; the calculation is based on the resolved crystal structure.

In still another embodiment of this aspect of the invention, Form C has characteristic PXRD peaks as shown in FIG. 3.

In still another embodiment of this aspect of the invention, Form C has a crystalline structure as defined in Table 3.

TABLE 3

| Crystal Structure of Form C | |
|---|---|
| Crystal Form | Form C |
| Lattice Type | Triclinic |
| Space Group | P1 |
| a (Å) | 8 |
| b (Å) | 9 |
| c (Å) | 16 |
| α (°) | 100 |
| β (°) | 99 |
| γ (°) | 111 |
| Volume (Å³) | 979 |
| Z | 1 |

Without limiting this aspect of the invention to any particular theory or calculation, Form C typically contains about 2.5 molecules of water per molecule of Compound I.

In yet another aspect, the invention features another crystalline form of Compound I (hereinafter Form D), which has characteristic peaks in the PXRD pattern at values of two theta (° 2θ) of 11.6, 12.9, 13.1, 13.8, 14.5, 17.4, 19.0, 19.9, 24.8, and 27.1. Preferably, these peaks have higher intensities than other peaks in the PXRD pattern. Also preferably, these peaks have relative intensities of 21%, 100%, 70%, 34%, 23%, 27%, 28%, 36%, 21%, and 34%, respectively.

In one embodiment of this aspect of the invention, Form D has characteristic peaks in the PXRD pattern at values of two theta (° 2θ) of 11.59, 12.93, 13.08, 13.81, 14.53, 17.40, 18.98, 19.91, 24.79, and 27.14. Preferably, these peaks have higher intensities than other peaks in the PXRD pattern. Also preferably, these peaks have relative intensities of 21%, 100%, 70%, 34%, 23%, 27%, 28%, 36%, 21%, and 34%, respectively.

In another embodiment of this aspect of the invention, Form D has characteristic peaks in the PXRD pattern at values of two theta (° 2θ) of 10.4, 10.6, 11.6, 12.9, 13.1, 13.6, 13.8, 14.5, 17.4, 19.0, 19.9, 22.4, 23.6, 23.7, 24.8, 25.6, 26.0, 27.1, 27.8, and 30.5. Preferably, these peaks have higher intensities than other peaks in the PXRD pattern. Also preferably, these peaks have relative intensities of 17%, 20%, 21%, 100%, 70%, 16%, 34%, 23%, 27%, 28%, 36%, 14%, 12%, 16%, 21%, 15%, 18%, 34%, 15%, and 20%, respectively.

In another embodiment of this aspect of the invention, Form D has characteristic peaks in the PXRD pattern at values of two theta (° 2θ) of 10.41, 10.63, 11.59, 12.93, 13.08, 13.61, 13.81, 14.53, 17.40, 18.98, 19.91, 22.40, 23.58, 23.69, 24.79, 25.59, 26.04, 27.14, 27.77, and 30.50. Preferably, these peaks have higher intensities than other peaks in the PXRD pattern. Also preferably, these peaks have relative intensities of 17%, 20%, 21%, 100%, 70%, 16%, 34%, 23%, 27%, 28%, 36%, 14%, 12%, 16%, 21%, 15%, 18%, 34%, 15%, and 20%, respectively.

In another embodiment of this aspect of the invention, Form D has characteristic peaks in the PXRD pattern at values of two theta (° 2θ) of 10.4, 10.6, 11.6, 12.9, 13.1, 13.6, 13.8, 14.5, 15.1, 17.4, 18.0, 19.0, 19.5, 19.7, 19.9, 20.3, 20.8, 21.0, 21.3, 21.9, 22.4, 23.1, 23.6, 23.7, 23.8, 24.8, 25.6, 25.7, 26.0, 27.1, 27.8, 28.6, 30.5, and 31.7. Preferably, these peaks have higher intensities than other peaks in the PXRD pattern. Also preferably, these peaks have relative intensities of 17%, 20%, 21%, 100%, 70%, 16%, 34%, 23%, 6%, 27%, 5%, 28%, 9%, 10%, 36%, 6%, 6%, 5%, 10%, 12%, 14%, 9%, 12%, 16%, 9%, 21%, 15%, 7%, 18%, 34%, 15%, 6%, 20%, and 6%, respectively.

In another embodiment of this aspect of the invention, Form D has characteristic peaks in the PXRD pattern at values of two theta (° 2θ) of 10.41, 10.63, 11.59, 12.93, 13.08, 13.61, 13.81, 14.53, 15.15, 17.40, 18.03, 18.98, 19.51, 19.69, 19.91, 20.30, 20.83, 21.03, 21.35, 21.89, 22.40, 23.14, 23.58, 23.69, 23.84, 24.79, 25.59, 25.74, 26.04, 27.14, 27.77, 28.60, 30.50, and 31.68. Preferably, these peaks have higher intensities than other peaks in the PXRD pattern. Also preferably, these peaks have relative intensities of 17%, 20%, 21%, 100%, 70%, 16%, 34%, 23%, 6%, 27%, 5%, 28%, 9%, 10%, 36%, 6%, 6%, 5%, 10%, 12%, 14%, 9%, 12%, 16%, 9%, 21%, 15%, 7%, 18%, 34%, 15%, 6%, 20%, and 6%, respectively.

Figure 4:
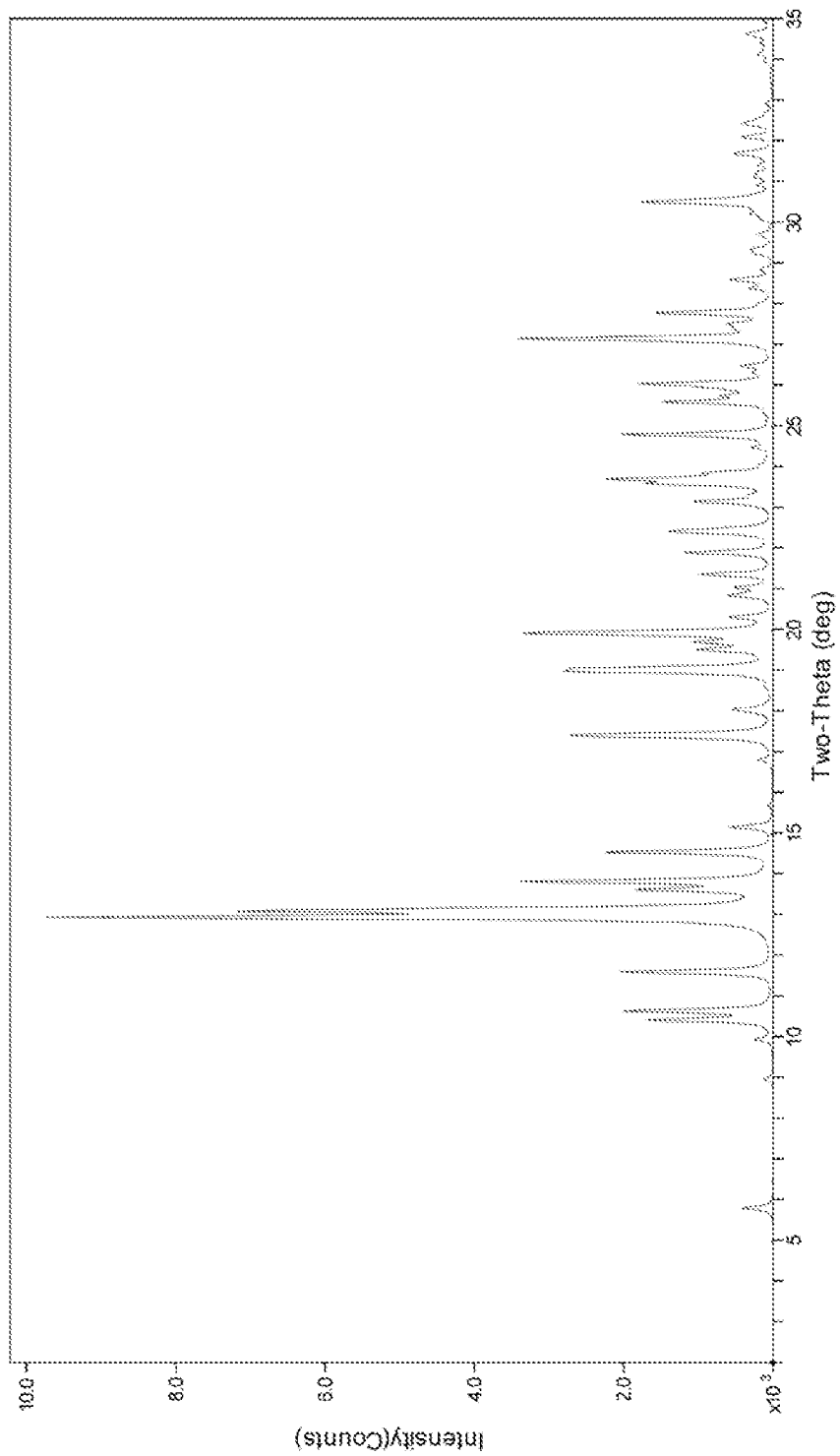
FIG. 4 describes the calculated PXRD pattern of Form D of Compound I; the calculation is based on the resolved crystal structure.

In still another embodiment of this aspect of the invention, Form D has characteristic PXRD peaks as shown in FIG. 4.

In still another embodiment of this aspect of the invention, Form D has a crystalline structure as defined in Table 4.

TABLE 4

| Crystal Structure of Form D | |
|---|---|
| Crystal Form | Form D |
| Lattice Type | Triclinic |
| Space Group | P1 |
| a (Å) | 10 |
| b (Å) | 14 |
| c (Å) | 16 |
| α (°) | 90 |
| β (°) | 73 |
| γ (°) | 76 |
| Volume (Å³) | 2008 |
| Z | 2 |

Without limiting this aspect of the invention to any particular theory or calculation, Form D typically contains about 2.75 molecules of water per molecule of Compound I.

In another aspect, the invention features another crystalline form of Compound I (hereinafter Form E), which has characteristic peaks in the PXRD pattern at values of two theta (° 2θ) of 10.6, 10.7, 11.6, 12.7, 13.0, 13.3, 13.8, 14.5, 19.0, and 23.4. Preferably, these peaks have higher intensities than other peaks in the PXRD pattern. Also preferably, these peaks have relative intensities of 35%, 35%, 39%, 100%, 82%, 85%, 49%, 36%, 40%, and 35%, respectively.

In one embodiment of this aspect of the invention, Form E has characteristic peaks in the PXRD pattern at values of two theta (° 2θ) of 10.60, 10.74, 11.55, 12.75, 12.95, 13.27, 13.82, 14.49, 18.96, and 23.39. Preferably, these peaks have higher intensities than other peaks in the PXRD pattern. Also preferably, these peaks have relative intensities of 35%, 35%, 39%, 100%, 82%, 85%, 49%, 36%, 40%, and 35%, respectively.

In another embodiment of this aspect of the invention, Form E has characteristic peaks in the PXRD pattern at values of two theta (° 2θ) of 10.6, 10.7, 11.6, 12.7, 13.0, 13.3, 13.6, 13.8, 14.5, 17.3, 18.7, 19.0, 20.1, 23.4, 23.9, 24.5, 25.2, 25.6, 26.8, and 27.3. Preferably, these peaks have higher intensities than other peaks in the PXRD pattern. Also preferably, these peaks have relative intensities of 35%, 35%, 39%, 100%, 82%, 85%, 22%, 49%, 36%, 25%, 29%, 40%, 28%, 35%, 25%, 29%, 25%, 23%, 27%, and 26%, respectively.

In another embodiment of this aspect of the invention, Form E has characteristic peaks in the PXRD pattern at values of two theta (° 2θ) of 10.60, 10.74, 11.55, 12.75, 12.95, 13.27, 13.59, 13.82, 14.49, 17.32, 18.68, 18.96, 20.10, 23.39, 23.88, 24.46, 25.17, 25.56, 26.80, and 27.28. Preferably, these peaks have higher intensities than other peaks in the PXRD pattern. Also preferably, these peaks have relative intensities of 35%, 35%, 39%, 100%, 82%, 85%, 22%, 49%, 36%, 25%, 29%, 40%, 28%, 35%, 25%, 29%, 25%, 23%, 27%, and 26%, respectively.

In another embodiment of this aspect of the invention, Form E has characteristic peaks in the PXRD pattern at values of two theta (° 2θ) of 5.8, 10.6, 10.7, 11.6, 12.7, 13.0, 13.3, 13.6, 13.8, 14.5, 14.9, 17.3, 17.5, 17.9, 18.7, 19.0, 19.7, 19.9, 20.1, 20.6, 21.5, 22.0, 22.5, 22.9, 23.4, 23.9, 24.5, 25.2, 25.6, 26.0, 26.8, 27.3, and 30.1. Preferably, these peaks have higher intensities than other peaks in the PXRD pattern. Also preferably, these peaks have relative intensities of 6%, 35%, 35%, 39%, 100%, 82%, 85%, 22%, 49%, 36%, 7%, 25%, 17%, 11%, 29%, 40%, 8%, 16%, 28%, 11%, 18%, 21%, 13%, 16%, 35%, 25%, 29%, 25%, 23%, 5%, 27%, 26%, and 12%, respectively.

In another embodiment of this aspect of the invention, Form E has characteristic peaks in the PXRD pattern at values of two theta (° 2θ) of 5.78, 10.60, 10.74, 11.55, 12.75, 12.95, 13.27, 13.59, 13.82, 14.49, 14.91, 17.32, 17.51, 17.90, 18.68, 18.96, 19.74, 19.92, 20.10, 20.59, 21.51, 21.99, 22.47, 22.93, 23.39, 23.88, 24.46, 25.17, 25.56, 25.99, 26.80, 27.28, and 30.11. Preferably, these peaks have higher intensities than other peaks in the PXRD pattern. Also preferably, these peaks have relative intensities of 6%, 35%, 35%, 39%, 100%, 82%, 85%, 22%, 49%, 36%, 7%, 25%, 17%, 11%, 29%, 40%, 8%, 16%, 28%, 11%, 18%, 21%, 13%, 16%, 35%, 25%, 29%, 25%, 23%, 5%, 27%, 26%, and 12%, respectively.

Figure 5:
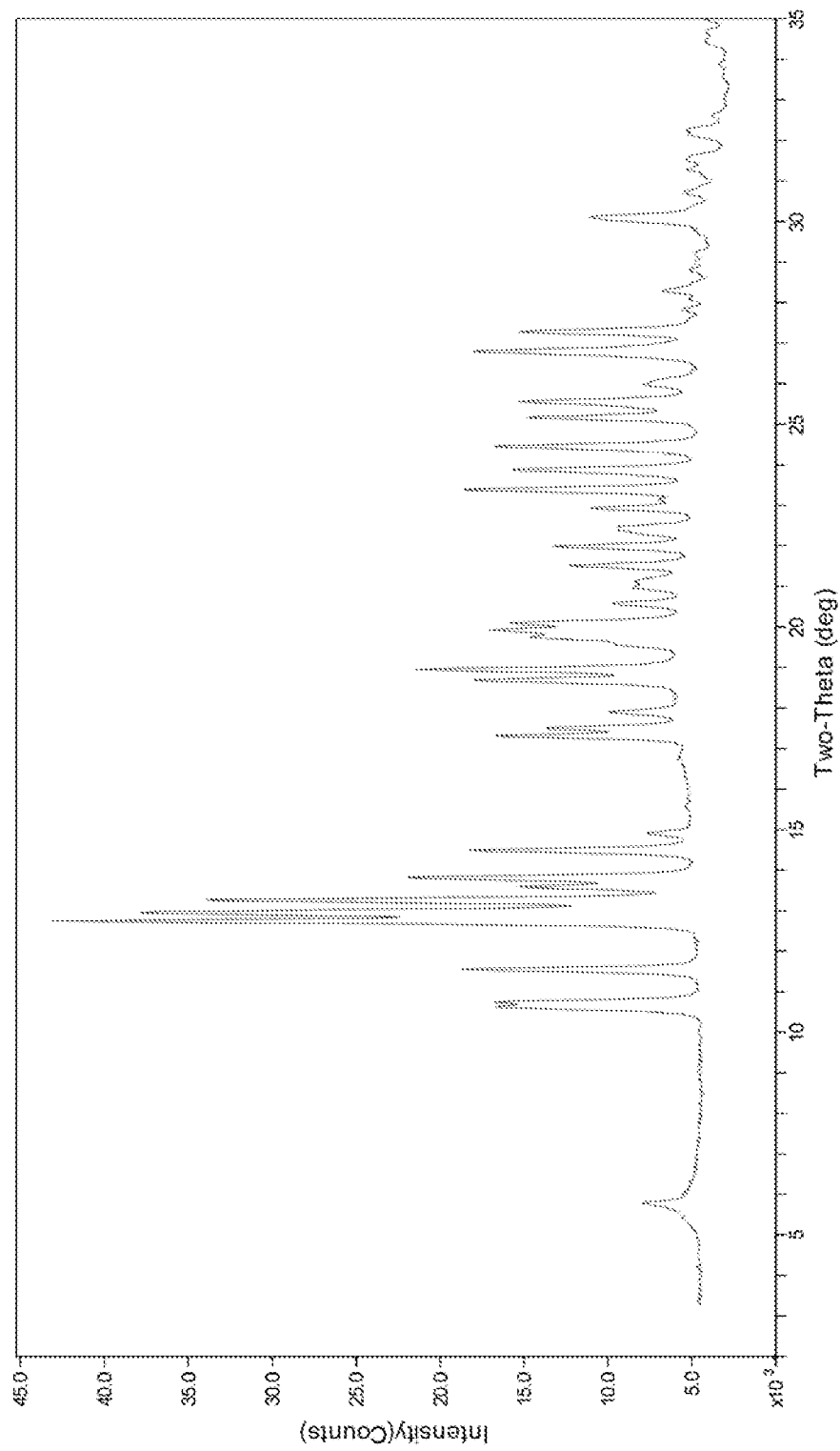
FIG. 5 shows the PXRD pattern of Form E of Compound I.

In still another embodiment of this aspect of the invention, Form E has characteristic PXRD peaks as shown in FIG. 5.

Without limiting this aspect of the invention to any particular theory or calculation, Form E typically contains from about 0 to about 3 molecules of water per molecule of Compound I, and may be formed by equilibrating a crystalline form of the invention (e.g., Form A, B, C, D, F, G, or H) at 11% relative humidity (RH).

In another aspect, the invention features another crystalline form of Compound I (hereinafter Form F), which has characteristic peaks in the PXRD pattern at values of two theta (° 2θ) of 10.7, 11.6, 12.7, 13.2, 13.6, 14.5, 17.4, 18.6, 19.0, 19.9, and 26.6. Preferably, these peaks have higher intensities than other peaks in the PXRD pattern. Also preferably, these peaks have relative intensities of 40%, 33%, 100%, 90%, 52%, 31%, 31%, 37%, 40%, 47%, and 34%, respectively.

In one embodiment of this aspect of the invention, Form F has characteristic peaks in the PXRD pattern at values of two theta (° 2θ) of 10.68, 11.57, 12.74, 13.16, 13.60, 14.47, 17.37, 18.64, 18.95, 19.92, and 26.59. Preferably, these peaks have higher intensities than other peaks in the PXRD pattern. Also preferably, these peaks have relative intensities of 40%, 33%, 100%, 90%, 52%, 31%, 31%, 37%, 40%, 47%, and 34%, respectively.

In another embodiment of this aspect of the invention, Form F has characteristic peaks in the PXRD pattern at values of two theta (° 2θ) of 10.5, 10.7, 11.6, 12.7, 13.2, 13.6, 14.5, 17.4, 18.6, 19.0, 19.9, 21.4, 21.9, 22.4, 23.3, 24.3, 25.2, 25.5, 26.6, 27.2, and 29.9. Preferably, these peaks have higher intensities than other peaks in the PXRD pattern. Also preferably, these peaks have relative intensities of 25%, 40%, 33%, 100%, 90%, 52%, 31%, 31%, 37%, 40%, 47%, 20%, 20%, 21%, 29%, 30%, 27%, 27%, 34%, 22%, and 21%, respectively.

In another embodiment of this aspect of the invention, Form F has characteristic peaks in the PXRD pattern at values of two theta (° 2θ) of 10.52, 10.68, 11.57, 12.74, 13.16, 13.60, 14.47, 17.37, 18.64, 18.95, 19.92, 21.39, 21.88, 22.41, 23.28, 24.30, 25.19, 25.54, 26.59, 27.22, and 29.91. Preferably, these peaks have higher intensities than other peaks in the PXRD pattern. Also preferably, these peaks have relative intensities of 25%, 40%, 33%, 100%, 90%, 52%, 31%, 31%, 37%, 40%, 47%, 20%, 20%, 21%, 29%, 30%, 27%, 27%, 34%, 22%, and 21%, respectively.

In another embodiment of this aspect of the invention, Form F has characteristic peaks in the PXRD pattern at values of two theta (° 2θ) of 5.8, 10.5, 10.7, 11.6, 12.7, 13.2, 13.6, 14.5, 14.9, 17.4, 17.9, 18.6, 19.0, 19.7, 19.9, 20.4, 20.8, 21.4, 21.9, 22.4, 23.0, 23.3, 23.5, 23.8, 24.3, 25.2, 25.5, 26.6, 27.2, 28.4, and 29.9. Preferably, these peaks have higher intensities than other peaks in the PXRD pattern. Also preferably, these peaks have relative intensities of 9%, 25%, 40%, 33%, 100%, 90%, 52%, 31%, 8%, 31%, 11%, 37%, 40%, 9%, 47%, 12%, 10%, 20%, 20%, 21%, 13%, 29%, 6%, 14%, 30%, 27%, 27%, 34%, 22%, 8%, and 21%, respectively.

In another embodiment of this aspect of the invention, Form F has characteristic peaks in the PXRD pattern at values of two theta (° 2θ) of 5.78, 10.52, 10.68, 11.57, 12.74, 13.16, 13.60, 14.47, 14.86, 17.37, 17.94, 18.64, 18.95, 19.71, 19.92, 20.40, 20.78, 21.39, 21.88, 22.41, 23.00, 23.28, 23.52, 23.81, 24.30, 25.19, 25.54, 26.59, 27.22, 28.39, and 29.91. Preferably, these peaks have higher intensities than other peaks in the PXRD pattern. Also preferably, these peaks have relative intensities of 9%, 25%, 40%, 33%, 100%, 90%, 52%, 31%, 8%, 31%, 11%, 37%, 40%, 9%, 47%, 12%, 10%, 20%, 20%, 21%, 13%, 29%, 6%, 14%, 30%, 27%, 27%, 34%, 22%, 8%, and 21%, respectively.

Figure 6:
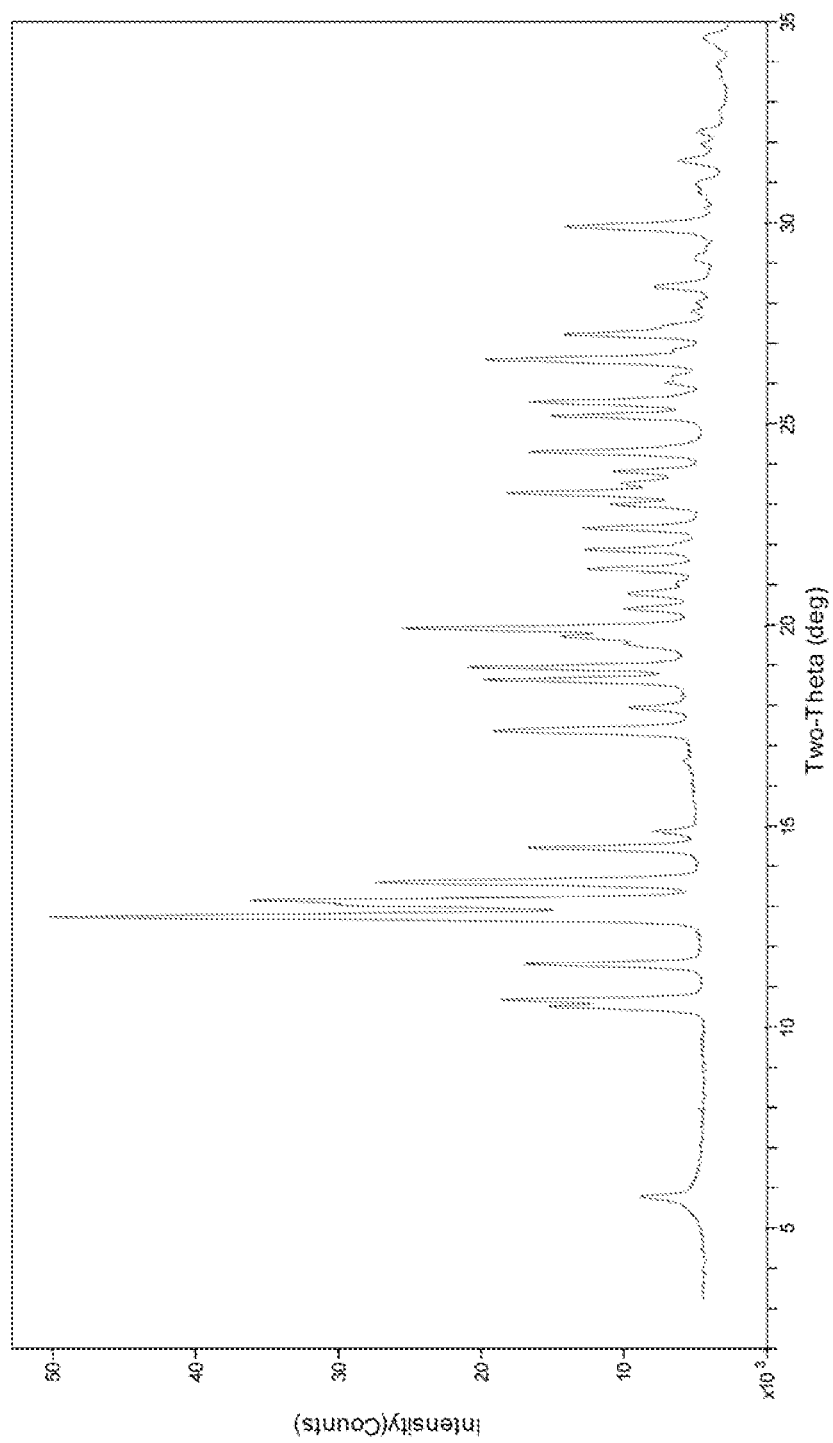
FIG. 6 shows the PXRD pattern of Form F of Compound I.

In still another embodiment of this aspect of the invention, Form F has characteristic PXRD peaks as shown in FIG. 6.

Without limiting this aspect of the invention to any particular theory or calculation, Form F typically contains from about 0 to about 3 molecules of water per molecule of Compound I, and can be formed by equilibrating a crystalline form of the invention (e.g., Form A, B, C, D, E, G or H) at 33% relative humidity.

In another aspect, the invention features another crystalline form of Compound I (hereinafter Form G), which has characteristic peaks in the PXRD pattern at values of two theta (° 2θ) of 10.7, 11.6, 12.7, 13.0, 13.2, 13.7, 14.5, 18.7, 19.0, and 19.9. Preferably, these peaks have higher intensities than other peaks in the PXRD pattern. Also preferably, these peaks have relative intensities of 36%, 34%, 100%, 102%, 75%, 37%, 31%, 32%, 38%, and 42%, respectively.

In one embodiment of this aspect of the invention, Form G has characteristic peaks in the PXRD pattern at values of two theta (° 2θ) of 10.70, 11.57, 12.75, 13.02, 13.18, 13.66, 14.47, 18.66, 18.96, and 19.94. Preferably, these peaks have higher intensities than other peaks in the PXRD pattern. Also preferably, these peaks have relative intensities of 36%, 34%, 100%, 102%, 75%, 37%, 31%, 32%, 38%, and 42%, respectively.

In another embodiment of this aspect of the invention, Form G has characteristic peaks in the PXRD pattern at values of two theta (° 2θ) of 10.5, 10.7, 11.6, 12.7, 13.0, 13.2, 13.7, 14.5, 17.3, 18.7, 19.0, 19.9, 21.9, 23.3, 24.3, 25.2, 25.6, 26.6, 27.2, and 30.0. Preferably, these peaks have higher intensities than other peaks in the PXRD pattern. Also preferably, these peaks have relative intensities of 24%, 36%, 34%, 100%, 102%, 75%, 37%, 31%, 30%, 32%, 38%, 42%, 18%, 27%, 26%, 24%, 24%, 27%, 18%, and 18%, respectively.

In another embodiment of this aspect of the invention, Form G has characteristic peaks in the PXRD pattern at values of two theta (° 2θ) of 10.54, 10.70, 11.57, 12.75, 13.02, 13.18, 13.66, 14.47, 17.35, 18.66, 18.96, 19.94, 21.90, 23.31, 24.34, 25.19, 25.56, 26.64, 27.24, and 29.95. Preferably, these peaks have higher intensities than other peaks in the PXRD pattern. Also preferably, these peaks have relative intensities of 24%, 36%, 34%, 100%, 102%, 75%, 37%, 31%, 30%, 32%, 38%, 42%, 18%, 27%, 26%, 24%, 24%, 27%, 18%, and 18%, respectively.

In another embodiment of this aspect of the invention, Form G has characteristic peaks in the PXRD pattern at values of two theta (° 2θ) of 5.8, 10.5, 10.7, 11.6, 12.7, 13.0, 13.2, 13.7, 14.5, 14.9, 17.3, 17.9, 18.7, 19.0, 19.7, 19.9, 20.5, 20.9, 21.4, 21.9, 22.4, 23.0, 23.3, 23.8, 24.3, 25.2, 25.6, 26.6, 27.2, and 30.0. Preferably, these peaks have higher intensities than other peaks in the PXRD pattern. Also preferably, these peaks have relative intensities of 7%, 24%, 36%, 34%, 100%, 102%, 75%, 37%, 31%, 7%, 30%, 9%, 32%, 38%, 8%, 42%, 9%, 6%, 17%, 18%, 16%, 13%, 27%, 10%, 26%, 24%, 24%, 27%, 18%, and 18%, respectively.

In another embodiment of this aspect of the invention, Form G has characteristic peaks in the PXRD pattern at values of two theta (° 2θ) of 5.80, 10.54, 10.70, 11.57, 12.75, 13.02, 13.18, 13.66, 14.47, 14.88, 17.35, 17.92, 18.66, 18.96, 19.69, 19.94, 20.45, 20.86, 21.42, 21.90, 22.41, 22.98, 23.31, 23.84, 24.34, 25.19, 25.56, 26.64, 27.24, and 29.95. Preferably, these peaks have higher intensities than other peaks in the PXRD pattern. Also preferably, these peaks have relative intensities of 7%, 24%, 36%, 34%, 100%, 102%, 75%, 37%, 31%, 7%, 30%, 9%, 32%, 38%, 8%, 42%, 9%, 6%, 17%, 18%, 16%, 13%, 27%, 10%, 26%, 24%, 24%, 27%, 18%, and 18%, respectively.

Figure 7:
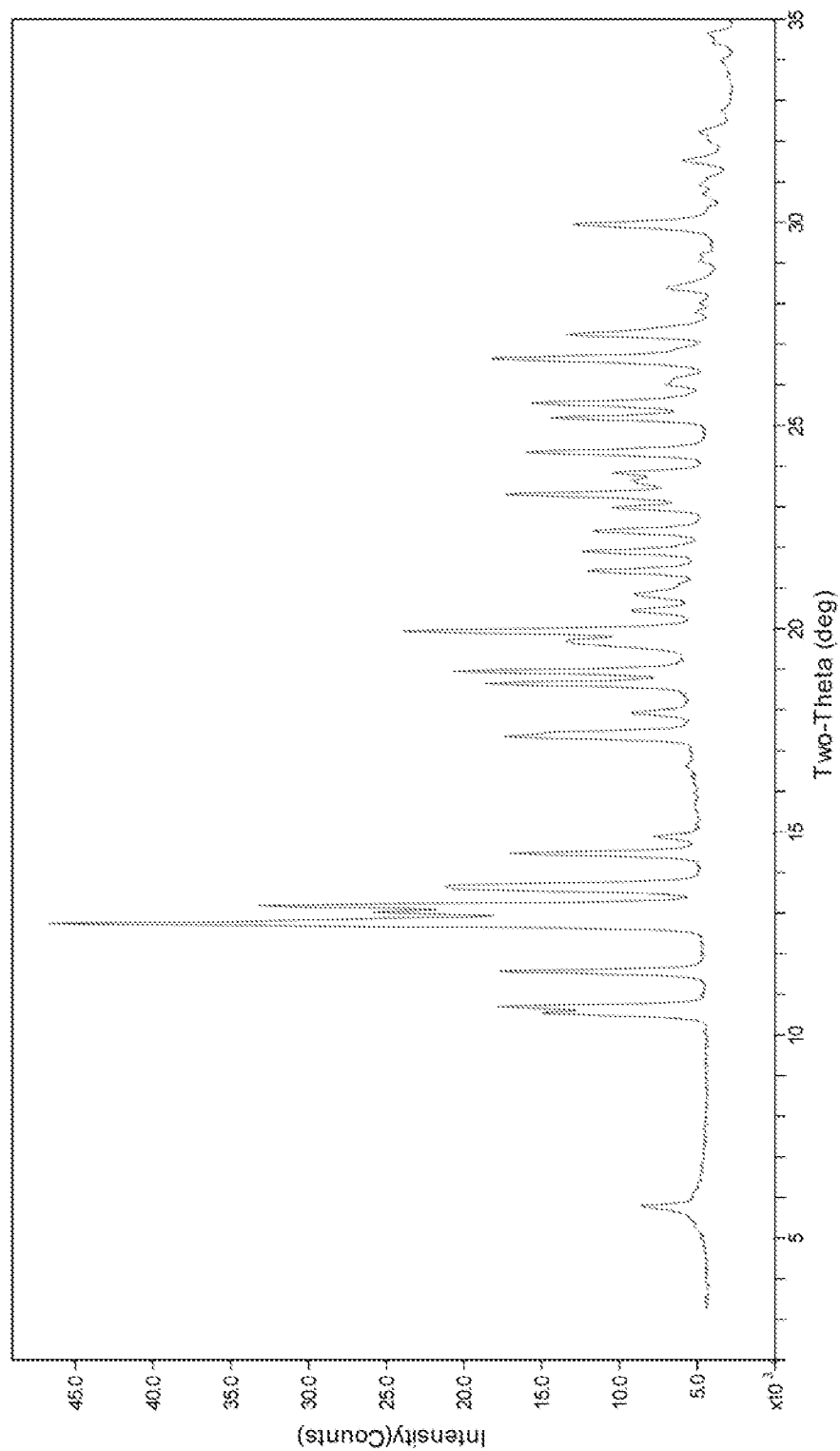
FIG. 7 illustrates the PXRD pattern of Form G of Compound I.

In still another embodiment of this aspect of the invention, Form G has characteristic PXRD peaks as shown in FIG. 7.

Without limiting this aspect of the invention to any particular theory or calculation, Form G typically contain from about 0 to about 3 molecules of water per molecule of Compound I, and can be formed by equilibrating a crystalline form of the invention (e.g., Form A, B, C, D, E, F, or H) at 43% relative humidity.

In another aspect, the invention features another crystalline form of Compound I (hereinafter Form H), which has characteristic peaks in the PXRD pattern at values of two theta (° 2θ) of 10.7, 12.7, 13.1, 13.6, 17.4, 18.6, 19.0, 19.8, 23.3, 25.6, and 26.5. Preferably, these peaks have higher intensities than other peaks in the PXRD pattern. Also preferably, these peaks have relative intensities of 29%, 100%, 70%, 53%, 32%, 24%, 30%, 27%, 27%, 24%, and 30%, respectively.

In one embodiment of this aspect of the invention, Form H has characteristic peaks in the PXRD pattern at values of two theta (° 2θ) of 10.66, 12.75, 13.09, 13.57, 17.37, 18.62, 18.96, 19.83, 23.26, 25.55, and 26.52. Preferably, these peaks have higher intensities than other peaks in the PXRD pattern. Also preferably, these peaks have relative intensities of 29%, 100%, 70%, 53%, 32%, 24%, 30%, 27%, 27%, 24%, and 30%, respectively.

In another embodiment of this aspect of the invention, Form H has characteristic peaks in the PXRD pattern at values of two theta (° 2θ) of 10.5, 10.7, 11.6, 12.7, 13.1, 13.6, 14.5, 17.4, 18.6, 19.0, 19.8, 21.3, 21.8, 22.4, 23.3, 24.2, 25.2, 25.6, 26.5, 27.2, and 29.8. Preferably, these peaks have higher intensities than other peaks in the PXRD pattern. Also preferably, these peaks have relative intensities of 20%, 29%, 22%, 100%, 70%, 53%, 23%, 32%, 24%, 30%, 27%, 15%, 14%, 14%, 27%, 21%, 21%, 24%, 30%, 18%, and 19%, respectively.

In another embodiment of this aspect of the invention, Form H has characteristic peaks in the PXRD pattern at values of two theta (° 2θ) of 10.47, 10.66, 11.58, 12.75, 13.09, 13.57, 14.45, 17.37, 18.62, 18.96, 19.83, 21.35, 21.83, 22.41, 23.26, 24.25, 25.21, 25.55, 26.52, 27.21, and 29.84. Preferably, these peaks have higher intensities than other peaks in the PXRD pattern. Also preferably, these peaks have relative intensities of 20%, 29%, 22%, 100%, 70%, 53%, 23%, 32%, 24%, 30%, 27%, 15%, 14%, 14%, 27%, 21%, 21%, 24%, 30%, 18%, and 19%, respectively.

In another embodiment of this aspect of the invention, Form H has characteristic peaks in the PXRD pattern at values of two theta (° 2θ) of 5.8, 10.5, 10.7, 11.6, 12.7, 13.1, 13.6, 14.5, 14.9, 17.4, 18.0, 18.6, 19.0, 19.4, 19.8, 20.4, 20.7, 21.3, 21.8, 22.4, 23.0, 23.3, 23.8, 24.2, 25.2, 25.6, 26.5, 27.2, and 29.8. Preferably, these peaks have higher intensities than other peaks in the PXRD pattern. Also preferably, these peaks have relative intensities of 9%, 20%, 29%, 22%, 100%, 70%, 53%, 23%, 6%, 32%, 7%, 24%, 30%, 7%, 27%, 9%, 8%, 15%, 14%, 14%, 13%, 27%, 10%, 21%, 21%, 24%, 30%, 18%, and 19%, respectively.

In another embodiment of this aspect of the invention, Form H has characteristic peaks in the PXRD pattern at values of two theta (° 2θ) of 5.80, 10.47, 10.66, 11.58, 12.75, 13.09, 13.57, 14.45, 14.86, 17.37, 17.96, 18.62, 18.96, 19.40, 19.83, 20.36, 20.69, 21.35, 21.83, 22.41, 23.03, 23.26, 23.81, 24.25, 25.21, 25.55, 26.52, 27.21, and 29.84. Preferably, these peaks have higher intensities than other peaks in the PXRD pattern. Also preferably, these peaks have relative intensities of 9%, 20%, 29%, 22%, 100%, 70%, 53%, 23%, 6%, 32%, 7%, 24%, 30%, 7%, 27%, 9%, 8%, 15%, 14%, 14%, 13%, 27%, 10%, 21%, 21%, 24%, 30%, 18%, and 19%, respectively.

Figure 8:
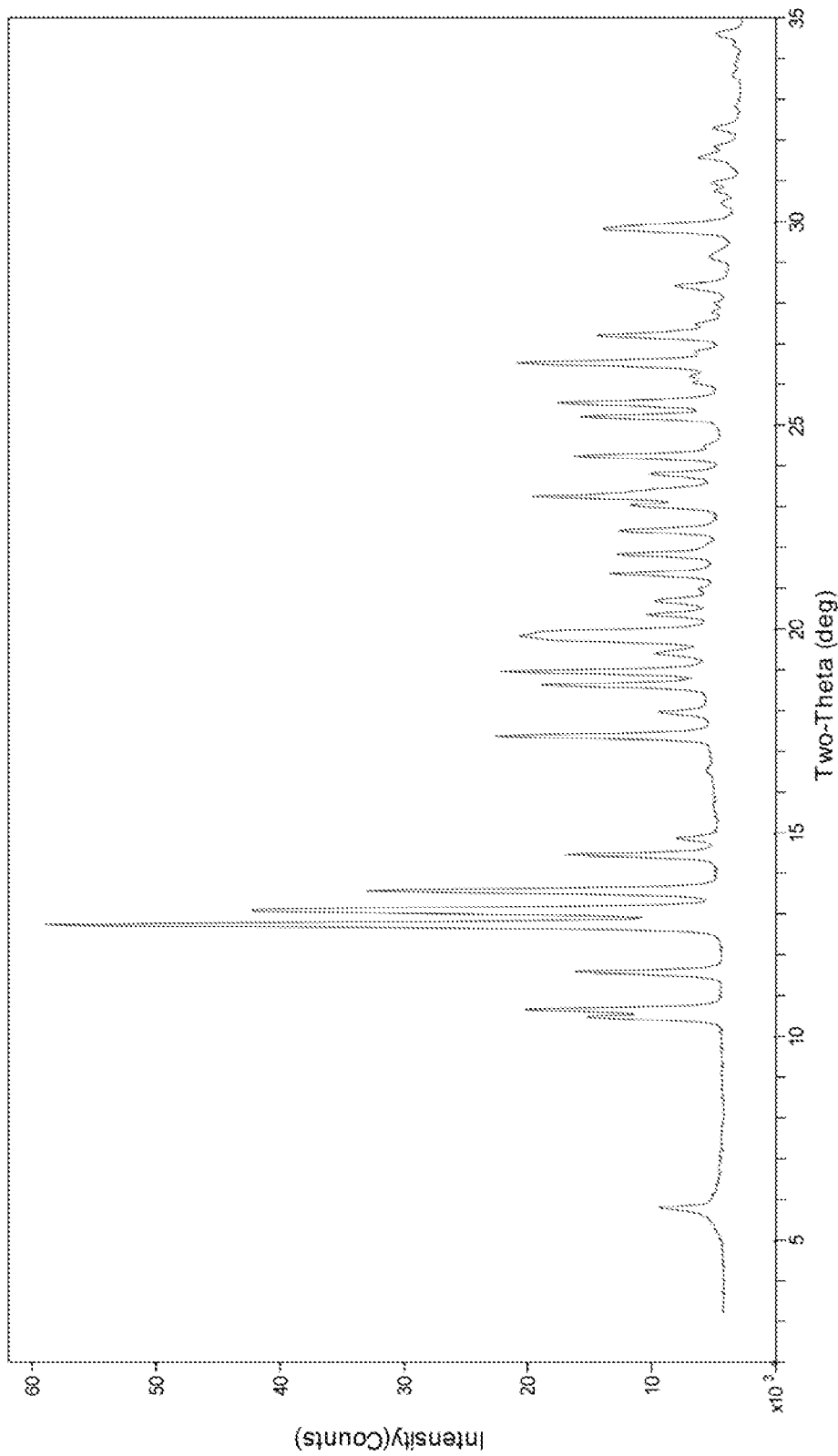
FIG. 8 depicts the PXRD pattern of Form H of Compound I.

In still another embodiment of this aspect of the invention, Form H has characteristic PXRD peaks as shown in FIG. 8.

Without limiting this aspect of the invention to any particular theory or calculation, Form H typically contains from about 0 to about 3 molecules of water per molecule of Compound I, and can be formed by equilibrating a crystalline form of the invention (e.g., Form A, B, C, D, E, F or G) at 76% relative humidity.

In still another aspect, the present invention features a crystalline form of Compound I (hereinafter Class 2), wherein when the crystalline form is equilibrated at 43% relative humidity, it has characteristic peaks in the PXRD pattern as Form G. For example, a Class 2 crystal, upon being equilibrated at 43% relative humidity, can have characteristic peaks in the PXRD pattern at values of two theta (° 2θ) of 10.7, 11.6, 12.7, 13.0, 13.2, 13.7, 14.5, 18.7, 19.0, and 19.9. Preferably, these peaks have higher intensities than other peaks in the PXRD pattern. Also preferably, these peaks have relative intensities of 36%, 34%, 100%, 102%, 75%, 37%, 31%, 32%, 38%, and 42%, respectively. As non-limiting examples, Forms A, B, C, D, E, F, G and H are Class 2 of the crystalline form of Compound I.

In one embodiment of this aspect of the invention, Class 2 of the crystalline form of Compound I has characteristic peaks in the PXRD pattern at values of two theta (° 2θ) of 10.70, 11.57, 12.75, 13.02, 13.18, 13.66, 14.47, 18.66, 18.96, and 19.94 after equilibration at 43% relative humidity. Preferably, these peaks have higher intensities than other peaks in the PXRD pattern. Also preferably, these peaks have relative intensities of 36%, 34%, 100%, 102%, 75%, 37%, 31%, 32%, 38%, and 42%, respectively.

In another embodiment of this aspect of the invention, Class 2 of the crystalline form of Compound I has characteristic peaks in the PXRD pattern at values of two theta (° 2θ) of 10.5, 10.7, 11.6, 12.7, 13.0, 13.2, 13.7, 14.5, 17.3, 18.7, 19.0, 19.9, 21.9, 23.3, 24.3, 25.2, 25.6, 26.6, 27.2, and 30.0 after equilibration at 43% relative humidity. Preferably, these peaks have higher intensities than other peaks in the PXRD pattern. Also preferably, these peaks have relative intensities of 24%, 36%, 34%, 100%, 102%, 75%, 37%, 31%, 30%, 32%, 38%, 42%, 18%, 27%, 26%, 24%, 24%, 27%, 18%, and 18%, respectively.

In another embodiment of this aspect of the invention, Class 2 of the crystalline form of Compound I has characteristic peaks in the PXRD pattern at values of two theta (° 2θ) of 10.54, 10.70, 11.57, 12.75, 13.02, 13.18, 13.66, 14.47, 17.35, 18.66, 18.96, 19.94, 21.90, 23.31, 24.34, 25.19, 25.56, 26.64, 27.24, and 29.95 after equilibration at 43% relative humidity. Preferably, these peaks have higher intensities than other peaks in the PXRD pattern. Also preferably, these peaks have relative intensities of 24%, 36%, 34%, 100%, 102%, 75%, 37%, 31%, 30%, 32%, 38%, 42%, 18%, 27%, 26%, 24%, 24%, 27%, 18%, and 18%, respectively.

In another embodiment of this aspect of the invention, Class 2 of the crystalline form of Compound I has characteristic peaks in the PXRD pattern at values of two theta (° 2θ) of 5.8, 10.5, 10.7, 11.6, 12.7, 13.0, 13.2, 13.7, 14.5, 14.9, 17.3, 17.9, 18.7, 19.0, 19.7, 19.9, 20.5, 20.9, 21.4, 21.9, 22.4, 23.0, 23.3, 23.8, 24.3, 25.2, 25.6, 26.6, 27.2, and 30.0 after equilibration at 43% relative humidity. Preferably, these peaks have higher intensities than other peaks in the PXRD pattern. Also preferably, these peaks have relative intensities of 7%, 24%, 36%, 34%, 100%, 102%, 75%, 37%, 31%, 7%, 30%, 9%, 32%, 38%, 8%, 42%, 9%, 6%, 17%, 18%, 16%, 13%, 27%, 10%, 26%, 24%, 24%, 27%, 18%, and 18%, respectively.

In another embodiment of this aspect of the invention, Class 2 of the crystalline form of Compound I has characteristic peaks in the PXRD pattern at values of two theta (° 2θ) of 5.80, 10.54, 10.70, 11.57, 12.75, 13.02, 13.18, 13.66, 14.47, 14.88, 17.35, 17.92, 18.66, 18.96, 19.69, 19.94, 20.45, 20.86, 21.42, 21.90, 22.41, 22.98, 23.31, 23.84, 24.34, 25.19, 25.56, 26.64, 27.24, and 29.95 after equilibration at 43% relative humidity. Preferably, these peaks have higher intensities than other peaks in the PXRD pattern. Also preferably, these peaks have relative intensities of 7%, 24%, 36%, 34%, 100%, 102%, 75%, 37%, 31%, 7%, 30%, 9%, 32%, 38%, 8%, 42%, 9%, 6%, 17%, 18%, 16%, 13%, 27%, 10%, 26%, 24%, 24%, 27%, 18%, and 18%, respectively.

In still another embodiment of this aspect of the invention, Class 2 of the crystalline form of Compound I has characteristic PXRD peaks as shown in FIG. 7 after equilibration at 43% relative humidity.

As used herein, equilibration at a specific relative humidity can be achieved by the following process. A crystalline solid is packed in 0.0395 inch internal diameter polyimide capillaries (one end open and the other sealed). The capillaries are equilibrated in a relative humidity (RH) chamber for 3-4 weeks at a specific relative humidity. As appreciated by one of ordinary skill in the art, 11% RH can be obtained by equilibrating against lithium chloride saturated solution; 33% RH can be obtained by equilibrating against magnesium chloride saturated solution; 43% RH can be obtained by equilibrating against potassium carbonate; and 76% RH can be obtained by equilibrating against sodium acetate. After 3-4 weeks of equilibration, the open ends of the capillaries are quickly sealed. PXRD data can be collected in transmission mode through the capillary, which can be rotated to minimize preferred orientation effects. Acquisition time on INEL is typically 2 hours for each sample.

As used herein, PXRD data can be collected using a G3000 diffractometer (Inel Corp., Artenay, France) equipped with a curved position-sensitive detector and parallel-beam optics. The diffractometer is operated with a copper anode tube (1.5 kW fine focus) at 40 kV and 30 mA. An incident-beam germanium monochromator provides monochromatic Cu—$K_\alpha$ radiation, which has a wavelength of 1.54178 Å. The diffractometer can be calibrated using the attenuated direct beam at one-degree intervals. Calibration can be checked using a silicon powder line position reference standard (NIST 640c). The instrument can be computer-controlled using Symphonix software (Inel Corp., Artenay, France) and the data can be analyzed using Jade software (version 6.5, Materials Data, Inc., Livermore, Calif.). The sample can be loaded onto an aluminum sample holder and leveled with a glass slide. PXRD peak position measurements are typically ±0.2 degrees two-theta (° 2θ).

In another aspect, the present invention features a crystalline form described above which is substantially pure. As used herein, the term "substantially pure", when used in reference to a given crystalline form, refers to the crystalline form which is at least 90% pure. This means that the crystalline form does not contain more than 10% of any other form of Compound I. More preferably, the term "substantially pure" refers to a crystalline form of Compound I which is at least 95% pure. This means that the crystalline form of Compound I does not contain more than 5% of any other form of Compound I. Even more preferably, the term "substantially pure" refers to a crystalline form of Compound I which is at least 97% pure. This means that the crystalline form of Compound I does not contain more than 3% of any other form of Compound I.

In one embodiment, the present invention feature Form A of Compound I which is substantially pure. Any Form A described above can be substantially pure, such as at least 90% pure, preferably at least 95% pure, or more preferably at least 97%.

In another embodiment, the present invention feature Form B of Compound I which is substantially pure. Any Form B described above can be substantially pure, such as at least 90% pure, preferably at least 95% pure, or more preferably at least 97%.

In another embodiment, the present invention feature Form C of Compound I which is substantially pure. Any Form C described above can be substantially pure, such as at least 90% pure, preferably at least 95% pure, or more preferably at least 97%.

In another embodiment, the present invention feature Form D of Compound I which is substantially pure. Any Form D described above can be substantially pure, such as at least 90% pure, preferably at least 95% pure, or more preferably at least 97%.

In another embodiment, the present invention feature Form E of Compound I which is substantially pure. Any Form E described above can be substantially pure, such as at least 90% pure, preferably at least 95% pure, or more preferably at least 97%.

In another embodiment, the present invention feature Form F of Compound I which is substantially pure. Any Form F described above can be substantially pure, such as at least 90% pure, preferably at least 95% pure, or more preferably at least 97%.

In another embodiment, the present invention feature Form G of Compound I which is substantially pure. Any Form G described above can be substantially pure, such as at least 90% pure, preferably at least 95% pure, or more preferably at least 97%.

In another embodiment, the present invention feature Form H of Compound I which is substantially pure. Any Form H described above can be substantially pure, such as at least 90% pure, preferably at least 95% pure, or more preferably at least 97%.

In another embodiment, the present invention feature Class 2 of Compound I which is substantially pure. Any Class 2 described above can be substantially pure, such as at least 90% pure, preferably at least 95% pure, or more preferably at least 97%.

In yet another aspect, the present invention features processes of using a crystalline form of the invention (e.g., Form A, B, C, D, E, F, G or H, or Class 2 of the crystalline form of Compound I) to make a composition comprising Compound I. The processes comprise dissolving a crystalline form of the invention in a solvent. Any crystalline form described hereinabove (e.g., any Class 2, or any Form A, B, C, D, E, F, G or H described herein) can be used in a process of the invention. Likewise, any polymer and surfactant described herein, or any combination thereof, can be used in a process described herein.

In one embodiment, the solvent is a volatile solvent such as ethanol or methanol. A suitable excipient, such as a hydrophilic polymer described below or a sugar alcohol, can also be dissolved in the solvent. The solution thus produced can then be dried to remove the solvent, such as via spray drying, freeze drying or other solvent evaporation techniques, thereby creating a solid dispersion that comprises Compound I and the excipient. Preferably, Compound I is in an amorphous form in the solid dispersion. More preferably, the solid dispersion is a solid solution or a glassy solution. In many cases, a pharmaceutically acceptable surfactant described below can also be added to the solution prior to solvent removal; and as a result, the solid dispersion/solid solution/glass solution produced according to this embodiment can also comprise a pharmaceutically acceptable surfactant.

In another embodiment, the solvent is an excipient, such as a hydrophilic polymer described below or a sugar alcohol, in a molten or rubbery state. The crystalline form of Compound I dissolves in the molten or rubbery excipient. Heating may be used to facilitate the dissolving and mixing of the crystalline form of Compound I in the molten or rubbery excipient. Preferably, melt extrusion is used to dissolve and mix the crystalline form of Compound I in the excipient. A solution or melt thus produced can be cooled and solidified to form a solid dispersion that comprises Compound I and the excipient. Preferably, Compound I is in an amorphous form in the solid dispersion. More preferably, the solid dispersion is a solid solution or a glassy solution. The solid dispersion, solid solution or glassy solution can be milled, ground or granulated, and then compressed into a tablet or another suitable solid dosage form with or without other additives. The solid dispersion, solid solution or glassy solution can also be directly shaped or configured into a tablet or another suitable solid dosage form. In many cases, a pharmaceutically acceptable surfactant described below can be added to the solution or melt prior to solidification; and as a result, the solid dispersion/solid solution/glassy solution produced according to this embodiment can also comprise a pharmaceutically acceptable surfactant.

In yet another embodiment, both heating and a volatile solvent are used to dissolve a crystalline form of Compound I in a solution comprising a suitable excipient.

As used herein, the term "solid dispersion" defines a system in a solid state (as opposed to a liquid or gaseous state) comprising at least two components, wherein one component is dispersed throughout the other component or components. For example, an active ingredient or a combination of active ingredients can be dispersed in a matrix comprised of a pharmaceutically acceptable hydrophilic polymer(s) and a pharmaceutically acceptable surfactant(s). The term "solid dispersion" encompasses systems having small particles of one phase dispersed in another phase. When a solid dispersion of the components is such that the system is chemically and physically uniform or homogenous throughout or consists of one phase (as defined in thermodynamics), such a solid dispersion is called a "solid solution." A glassy solution is a solid solution in which a solute is dissolved in a glassy solvent.

Non-limiting examples of excipients suitable for use in a process of the invention include numerous hydrophilic polymers. Preferably, a hydrophilic polymer employed in a process of the invention has a $T_g$ of at least 50° C., more preferably at least 60° C., and highly preferably at least 80° C. including, but not limited to, from 80° C. to 180° C., or from 100° C. to 150° C. Hydrophilic polymers with a $T_g$ described above can allow for the preparation of solid dispersions that are mechanically stable and, within ordinary temperature ranges, sufficiently temperature stable so that the solid dispersions can be used as dosage forms without further processing or be compacted to tablets with only a small amount of tabletting aids. Hydrophilic polymers having a $T_g$ of below 50° C. may also be used.

Preferably, a hydrophilic polymer employed in the present invention is water-soluble. A solid composition of the present invention can also comprise poorly water-soluble or water-insoluble polymer or polymers, such as cross-linked polymers. A hydrophilic polymer comprised in a solid composition of the present invention preferably has an apparent viscosity, when dissolved at 20° C. in an aqueous solution at 2% (w/v), of 1 to 5000 mPa·s, and more preferably of 1 to 700 mPa·s, and most preferably of 5 to 100 mPa·s.

Hydrophilic polymers suitable for use in a process of the invention include, but are not limited to, homopolymers or copolymers of N-vinyl lactams, such as homopolymers or copolymers of N-vinyl pyrrolidone (e.g., polyvinylpyrrolidone (PVP), or copolymers of N-vinyl pyrrolidone and vinyl acetate or vinyl propionate); cellulose esters or cellulose ethers, such as alkylcelluloses (e.g., methylcellulose or ethylcellulose), hydroxyalkylcelluloses (e.g., hydroxypropylcellulose), hydroxyalkylalkylcelluloses (e.g., hydroxypropylmethylcellulose), and cellulose phthalates or succinates (e.g., cellulose acetate phthalate and hydroxypropylmethylcellulose phthalate, hydroxypropylmethylcellulose succinate, or hydroxypropylmethylcellulose acetate succinate); high molecular polyalkylene oxides, such as polyethylene oxide, polypropylene oxide, and copolymers of ethylene oxide and propylene oxide; polyacrylates or polymethacrylates, such as methacrylic acid/ethyl acrylate copolymers, methacrylic acid/methyl methacrylate copolymers, butyl methacrylate/2-dimethylaminoethyl methacrylate copolymers, poly(hydroxyalkyl acrylates), and poly(hydroxyalkyl methacrylates); polyacrylamides; vinyl acetate polymers, such as copolymers of vinyl acetate and crotonic acid, and partially hydrolyzed polyvinyl acetate (also referred to as partially saponified "polyvinyl alcohol"); polyvinyl alcohol; oligo- or polysaccharides, such as carrageenans, galactomannans, and xanthan gum; polyhydroxyalkylacrylates; polyhydroxyalkyl-methacrylates; copolymers of methyl methacrylate and acrylic acid; polyethylene glycols (PEGs); or any mixture thereof.

Non-limiting examples of preferred hydrophilic polymers for use in a process of the invention include polyvinylpyrrolidone (PVP) K17, PVP K25, PVP K30, PVP K90, hydroxypropyl methylcellulose (HPMC) E3, HPMC E5, HPMC E6, HPMC E15, HPMC K3, HPMC A4, HPMC A15, HPMC acetate succinate (AS) LF, HPMC AS MF, HPMC AS HF, HPMC AS LG, HPMC AS MG, HPMC AS HG, HPMC phthalate (P) 50, HPMC P 55, Ethocel 4, Ethocel 7, Ethocel 10, Ethocel 14, Ethocel 20, copovidone (vinylpyrrolidone-vinyl acetate copolymer 60/40), polyvinyl acetate, methacrylate/methacrylic acid copolymer (Eudragit) L100-55, Eudragit L100, Eudragit S100, polyethylene glycol (PEG) 400, PEG 600, PEG 1450, PEG 3350, PEG 4000, PEG 6000, PEG 8000, poloxamer 124, poloxamer 188, poloxamer 237, poloxamer 338, and poloxamer 407.

Of these, homopolymers or copolymers of N-vinyl pyrrolidone, such as copolymers of N-vinyl pyrrolidone and vinyl acetate, are preferred. A non-limiting example of a preferred polymer is a copolymer of 60% by weight of N-vinyl pyrrolidone and 40% by weight of vinyl acetate. Other preferred polymers include, without limitation, hydroxypropyl methylcellulose (HPMC, also known as hypromellose in USP), such as hydroxypropyl methylcellulose grade E5 (HPMC-E5); and hydroxypropyl methylcellulose acetate succinate (HPMC-AS).

A pharmaceutically acceptable surfactant employed in a process of the invention is preferably a non-ionic surfactant. More preferably, the non-ionic surfactant has an HLB value of from 2-20. The HLB system (Fiedler, H. B., ENCYCLOPEDIA OF EXCIPIENTS, 5$^{th}$ ed., Aulendorf: ECV-Editio-Cantor-Verlag (2002)) attributes numeric values to surfactants, with lipophilic substances receiving lower HLB values and hydrophilic substances receiving higher HLB values.

Non-limiting examples of pharmaceutically acceptable surfactants that are suitable for use in a process of the invention include polyoxyethylene castor oil derivates, e.g. polyoxyethyleneglycerol triricinoleate or polyoxyl 35 castor oil (Cremophor® EL; BASF Corp.) or polyoxyethyleneglycerol oxystearate such as polyethylenglycol 40 hydrogenated castor oil (Cremophor® RH 40, also known as polyoxyl 40 hydrogenated castor oil or macrogolglycerol hydroxystearate) or polyethylenglycol 60 hydrogenated castor oil (Cremophor® RH 60); or a mono fatty acid ester of polyoxyethylene sorbitan, such as a mono fatty acid ester of polyoxyethylene (20) sorbitan, e.g. polyoxyethylene (20) sorbitan monooleate (Tween® 80), polyoxyethylene (20) sorbitan monostearate (Tween® 60), polyoxyethylene (20) sorbitan monopalmitate (Tween® 40), or polyoxyethylene (20) sorbitan monolaurate (Tween® 20). Other non-limiting examples of suitable surfactants include polyoxyethylene alkyl ethers, e.g. polyoxyethylene (3) lauryl ether, polyoxyethylene (5) cetyl ether, polyoxyethylene (2) stearyl ether, polyoxyethylene (5) stearyl ether; polyoxyethylene alkylaryl ethers, e.g. polyoxyethylene (2) nonylphenyl ether, polyoxyethylene (3) nonylphenyl ether, polyoxyethylene (4) nonylphenyl ether, polyoxyethylene (3) octylphenyl ether; polyethylene glycol fatty acid esters, e.g. PEG-200 monolaurate, PEG-200 dilaurate, PEG-300 dilaurate, PEG-400 dilaurate, PEG-300 distearate, PEG-300 dioleate; alkylene glycol fatty acid mono esters, e.g. propylene glycol monolaurate (Lauroglycol®); sucrose fatty acid esters, e.g. sucrose monostearate, sucrose distearate, sucrose monolaurate, sucrose dilaurate; sorbitan fatty acid mono esters such as sorbitan mono laurate (Span® 20), sorbitan monooleate, sorbitan monopalnitate (Span® 40), or sorbitan stearate. Other suitable surfactants include, but are not limited to, block copolymers of ethylene oxide and propylene oxide, also known as polyoxyethylene polyoxypropylene block copolymers or polyoxyethylene polypropyleneglycol, such as Poloxamer® 124, Poloxamer® 188, Poloxamer® 237, Poloxamer® 388, or Poloxamer® 407 (BASF Wyandotte Corp.).

Non-limiting examples of preferred surfactants for use in a process of the invention include polysorbate 20, polysorbate 40, polysorbate 60, polysorbate 80, Cremophor RH 40, Cremophor EL, Gelucire 44/14, Gelucire 50/13, D-alpha-tocopheryl polyethylene glycol 1000 succinate (vitamin E TPGS), propylene glycol laurate, sodium lauryl sulfate, and sorbitan monolaurate.

A pharmaceutically acceptable surfactant as used herein can be a mixture of pharmaceutically acceptable surfactants, such as a combination of a surfactant having an HLB value of below 10 and another surfactant having an HLB value of no lees than 10.

In one embodiment, a surfactant having an HLB value of at least 10 is used in a process of the invention. In another embodiment, a surfactant having an HLB value of below 10 is used in a process of the invention. In yet another embodiment, a mixture of two or more surfactants (e.g., a combination of one surfactant having an HLB value of at least 10 and another surfactant having an HLB value of below 10) is used in a process of the invention.

In one embodiment, a process of the invention comprises dissolving a crystalline form of the invention (e.g., Class 2 of the crystalline form of Compound I, or Form A, B, C, D, E, F, G or H), a hydrophilic polymer described above, and a surfactant described above to form a solution (e.g., a melt). The hydrophilic polymer can be selected, for example, from the group consisting of homopolymer of N-vinyl lactam, copolymer of N-vinyl lactam, cellulose ester, cellulose ether, polyalkylene oxide, polyacrylate, polymethacrylate, polyacrylamide, polyvinyl alcohol, vinyl acetate polymer, oligosaccharide, and polysaccharide. As a non-limiting example, the hydrophilic polymer is selected from the group consisting of homopolymer of N-vinyl pyrrolidone, copolymer of N-vinyl pyrrolidone, copolymer of N-vinyl pyrrolidone and vinyl acetate, copolymer of N-vinyl pyrrolidone and vinyl propionate, polyvinylpyrrolidone, methylcellulose, ethylcellulose, hydroxyalkylcelluloses, hydroxypropylcellulose, hydroxyalkylalkylcellulose, hydroxypropylmethylcellulose, cellulose phthalate, cellulose succinate, cellulose acetate phthalate, hydroxypropylmethylcellulose phthalate, hydroxypropylmethylcellulose succinate, hydroxypropylmethylcellulose acetate succinate, polyethylene oxide, polypropylene oxide, copolymer of ethylene oxide and propylene oxide, methacrylic acid/ethyl acrylate copolymer, methacrylic acid/methyl methacrylate copolymer, butyl methacrylate/2-dimethylaminoethyl methacrylate copolymer, poly(hydroxyalkyl acrylate), poly(hydroxyalkyl methacrylate), copolymer of vinyl acetate and crotonic acid, partially hydrolyzed polyvinyl acetate, carrageenan, galactomannan, and xanthan gum. Preferably, the hydrophilic polymer is selected from polyvinylpyrrolidone (PVP) K17, PVP K25, PVP K30, PVP K90, hydroxypropyl methylcellulose (HPMC) E3, HPMC E5, HPMC E6, HPMC E15, HPMC K3, HPMC A4, HPMC A15, HPMC acetate succinate (AS) LF, HPMC AS MF, HPMC AS HF, HPMC AS LG, HPMC AS MG, HPMC AS HG, HPMC phthalate (P) 50, HPMC P 55, Ethocel 4, Ethocel 7, Ethocel 10, Ethocel 14, Ethocel 20, copovidone (vinylpyrrolidone-vinyl acetate copolymer 60/40), polyvinyl acetate, methacrylate/methacrylic acid copolymer (Eudragit) L100-55, Eudragit L100, Eudragit S100, polyethylene glycol (PEG) 400, PEG 600, PEG 1450, PEG 3350, PEG 4000, PEG 6000, PEG 8000, poloxamer 124, poloxamer 188, poloxamer 237, poloxamer 338, or poloxamer 407. More preferably, the hydrophilic polymer is selected from homopolymers of vinylpyrrolidone (e.g., PVP with Fikentscher K values of from 12 to 100, or PVP with Fikentscher K values of from 17 to 30), or copolymers of 30 to 70% by weight of N-vinylpyrrolidone (VP) and 70 to 30% by weight of vinyl acetate (VA) (e.g., a copolymer of 60% by weight VP and 40% by weight VA). The surfactant can be selected, for example, from the group consisting of polyoxyethyleneglycerol triricinoleate or polyoxyl 35 castor oil (Cremophor® EL; BASF Corp.) or polyoxyethyleneglycerol oxystearate, mono fatty acid ester of polyoxyethylene sorbitan, polyoxyethylene alkyl ether, polyoxyethylene alkylaryl ether, polyethylene glycol fatty acid ester, alkylene glycol fatty acid mono ester, sucrose fatty acid ester, and sorbitan fatty acid mono ester. As a non-limited example, the surfactant is selected from the group consisting of polyethylenglycol 40 hydrogenated castor oil (Cremophor® RH 40, also known as polyoxyl 40 hydrogenated castor oil or macrogolglycerol hydroxystearate), polyethylenglycol 60 hydrogenated castor oil (Cremophor® RH 60), a mono fatty acid ester of polyoxyethylene (20) sorbitan (e.g. polyoxyethylene (20) sorbitan monooleate (Tween® 80), polyoxyethylene (20) sorbitan monostearate (Tween® 60), polyoxyethylene (20) sorbitan monopalmitate (Tween® 40), or polyoxyethylene (20) sorbitan monolaurate (Tween® 20)), polyoxyethylene (3) lauryl ether, polyoxyethylene (5) cetyl ether, polyoxyethylene (2) stearyl ether, polyoxyethylene (5) stearyl ether, polyoxyethylene (2) nonylphenyl ether, polyoxyethylene (3) nonylphenyl ether, polyoxyethylene (4) nonylphenyl ether, polyoxyethylene (3) octylphenyl ether, PEG-200 monolaurate, PEG-200 dilaurate, PEG-300 dilaurate, PEG-400 dilaurate, PEG-300 distearate, PEG-300 dioleate, propylene glycol monolaurate, sucrose monostearate, sucrose distearate, sucrose monolaurate, sucrose dilaurate, sorbitan monolaurate, sorbitan monooleate, sorbitan monopalnitate, and sorbitan stearate. Preferably, the surfactant is selected from polysorbate 20, polysorbate 40, polysorbate 60, polysorbate 80, Cremophor RH 40, Cremophor EL, Gelucire 44/14, Gelucire 50/13, D-alpha-tocopheryl polyethylene glycol 1000 succinate (vitamin E TPGS), propylene glycol laurate, sodium lauryl sulfate, or sorbitan monolaurate. More preferably, the surfactant is selected from sorbitan monolaurate or D-alpha-tocopheryl polyethylene glycol 1000 succinate.

In another embodiment, a process of the invention comprises dissolving a crystalline form of the invention (e.g., Class 2 of the crystalline form of Compound I, or Form A, B, C, D, E, F, G or H), a hydrophilic polymer described above, and a surfactant described above to form a solution (e.g., a melt). The hydrophilic polymer is a homopolymer or copolymer of N-vinyl pyrrolidone (e.g., copovidone). The pharmaceutically acceptable surfactant can be, e.g., vitamin E TPGS, or sorbitan monolaurate.

A melt-extrusion process of the invention typically comprises preparing a melt from (1) a crystalline form of the invention (e.g., Class 2, or Form A, B, C, D, E, F, G or H, of Compound I), (2) a hydrophilic polymer described above (or another suitable binder), and (3) preferably a surfactant described above. The melt can then be cooled until it solidifies. The crystalline form of Compound I initially used will disappear upon the formation of the melt. The melt may also include other additives. "Melting" means a transition into a liquid or rubbery state in which it is possible for one component to get embedded, preferably homogeneously embedded, in the other component or components. In many cases, the polymer component will melt and the other components including the crystalline form of Compound I and the surfactant will dissolve in the melt thereby forming a solution. Melting usually involves heating above the softening point of the polymer. The preparation of the melt can take place in a variety of ways. The mixing of the components can take place before, during or after the formation of the melt. For example, the components can be mixed first and then melted or be simultaneously mixed and melted. The melt can also be homogenized in order to disperse Compound I efficiently. In addition, it may be convenient first to melt the polymer and then to mix in and homogenize Compound I. In one example, all materials except the surfactant are blended and fed into an extruder, while the surfactant is molten externally and pumped in during extrusion.

In another example, the melt comprises Compound I and a hydrophilic polymer described above, and the melt temperature is in the range of from 100 to 170° C., preferably from 120 to 150° C., and highly preferably from 135 to 140° C. The melt can also include a pharmaceutically acceptable surfactant described above.

In still another example, the melt comprises Compound I, at least another anti-HCV agent (e.g., a HCV polymerase inhibitor, or a HCV NS5A inhibitor, or a combination of a HCV polymerase inhibitor and a HCV NS5A inhibitor), and a hydrophilic polymer described above. The melt can also include a pharmaceutically acceptable surfactant described above.

Preferably, a melt described herein also comprises ritonavir.

To start a melt-extrusion process, Compound I is employed in a crystalline form of the invention, e.g., Class 2, or Form A, B, C, D, E, F, G or H. A crystalline form of the invention may also be first dissolved in a suitable liquid solvent such as alcohols, aliphatic hydrocarbons, esters or, in some cases, liquid carbon dioxide; the solvent can be removed, e.g. evaporated, upon preparation of the melt.

Various additives can also be included in the melt, for example, flow regulators (e.g., colloidal silica), lubricants, fillers, disintegrants, plasticizers, colorants, or stabilizers (e.g., antioxidants, light stabilizers, radical scavengers, and stabilizers against microbial attack).

The melting and/or mixing can take place in an apparatus customary for this purpose. Particularly suitable ones are extruders or kneaders. Suitable extruders include single screw extruders, intermeshing screw extruders or multi-screw extruders, preferably twin screw extruders, which can be corotating or counterrotating and, optionally, be equipped with kneading disks. It will be appreciated that the working temperatures will be determined by the kind of extruder or the kind of configuration within the extruder that is used. Part of the energy needed to melt, mix and dissolve the components in the extruder can be provided by heating elements. However, the friction and shearing of the material in the extruder may also provide a substantial amount of energy to the mixture and aid in the formation of a homogeneous melt of the components.

The melt can range from thin to pasty to viscous. Shaping of the extrudate can be conveniently carried out by a calender with two counter-rotating rollers with mutually matching depressions on their surface. The extrudate can be cooled and allow to solidify. The extrudate can also be cut into pieces, either before (hot-cut) or after solidification (cold-cut).

The solidified extrusion product can be further milled, ground or otherwise reduced to granules. The solidified extrudate, as well as each granule produced, comprises a solid dispersion, preferably a solid solution, of Compound I in a matrix comprised of the hydrophilic polymer and optionally the pharmaceutically acceptable surfactant. Where the granules do not contain any surfactant, a pharmaceutically acceptable surfactant described above can be added to and blended with the granules. The extrusion product can also be blended with other active ingredient(s) (e.g., ritonavir) and/or additive(s) before being milled or ground to granules. The granules can be further processed into suitable solid oral dosage forms.

In one example, copovidone and a surfactant described above are mixed and granulated, followed by the addition of aerosil and a crystalline form of Compound I of the invention (e.g., Class 2, or Form A, B, C, D, E, F, G or H). The mixture can also contain ritonavir. The mixture, which may contain for example 5% by weight of Compound I, is then milled. The mixture is then subject to extrusion, and the extrudate thus produced can be milled and sieved for further processing to make capsules or tablets. The surfactant employed in this example can also be added through liquid dosing during extrusion.

The approach of solvent evaporation, e.g., via spray-drying, provides the advantage of allowing for processability at lower temperatures, if needed, and allows for other modifications to the process in order to further improve powder properties. The spray-dried powder can then be formulated further, if needed, and final drug product is flexible with regards to whether capsule, tablet or any other solid dosage form is desired.

Exemplary spray-drying processes and spray-drying equipment are described in K. Masters, SPRAY DRYING HANDBOOK (Halstead Press, New York, 4$^{th}$ ed., 1985). Non-limiting examples of spray-drying devices that are suitable for the present invention include spray dryers manufactured by Niro Inc. or GEA Process Engineering Inc., Buchi Labortechnik AG, and Spray Drying Systems, Inc. A spray-drying process generally involves breaking up a liquid mixture into small droplets and rapidly removing solvent from the droplets in a container (spray drying apparatus) where there is a strong driving force for evaporation of solvent from the droplets. Atomization techniques include, for example, two-fluid or pressure nozzles, or rotary atomizers. The strong driving force for solvent evaporation can be provided, for example, by maintaining the partial pressure of solvent in the spray drying apparatus well below the vapor pressure of the solvent at the temperatures of the drying droplets. This may be accomplished by either (1) maintaining the pressure in the spray drying apparatus at a partial vacuum; (2) mixing the liquid droplets with a warm drying gas (e.g., heated nitrogen); or (3) both.

The temperature and flow rate of the drying gas, as well as the spray dryer design, can be selected so that the droplets are dry enough by the time they reach the wall of the apparatus. This help to ensure that the dried droplets are essentially solid and can form a fine powder and do not stick to the apparatus wall. The spray-dried product can be collected by removing the material manually, pneumatically, mechanically or by other suitable means. The actual length of time to achieve the preferred level of dryness depends on the size of the droplets, the formulation, and spray dryer operation. Following the solidification, the solid powder may stay in the spray drying chamber for additional time (e.g., 5-60 seconds) to further evaporate solvent from the solid powder. The final solvent content in the solid dispersion as it exits the dryer is preferably at a sufficiently low level so as to improve the stability of the final product. For instance, the residual solvent content of the spray-dried powder can be less than 2% by weight. Highly preferably, the residual solvent content is within the limits set forth in the International Conference on Harmonization (ICH) Guidelines. In addition, it may be useful to subject the spray-dried composition to further drying to lower the residual solvent to even lower levels. Methods to further lower solvent levels include, but are not limited to, fluid bed drying, infra-red drying, tumble drying, vacuum drying, and combinations of these and other processes.

Like the solid extrudate described above, the spray dried product contains a solid dispersion, preferably a solid solution, of Compound I in a matrix comprised of a hydrophilic polymer described above and optionally a pharmaceutically acceptable surfactant described above. Where the spray dried product does not contain any surfactant, a pharmaceutically acceptable surfactant described above can be added to and blended with the spray-dried product before further processing.

Before feeding into a spray dryer, a crystalline form of Compound I of the invention (e.g., Class 2, or Form A, B, C, D, E, F, G or H), a hydrophilic polymer described above, as well as other optional active ingredients or excipients such as a pharmaceutically acceptable surfactant described above, can be dissolved in a solvent. Suitable solvents include, but are not limited to, alkanols (e.g., methanol, ethanol, 1-propanol, 2-propanol or mixtures thereof), acetone, acetone/water, alkanol/water mixtures (e.g., ethanol/water mixtures), or combinations thereof. The solution can also be preheated before being fed into the spray dryer. In many cases, ritonavir is dissolved together with the crystalline form of Compound I.

The solid dispersion produced by melt-extrusion, spray-drying or other techniques can be prepared into any suitable solid oral dosage forms. In one embodiment, the solid dispersion prepared by melt-extrusion, spray-drying or other techniques (e.g., the extrudate or the spray-dried powder) can be compressed into tablets. The solid dispersion can be either directly compressed, or milled or ground to granules or powders before compression. Compression can be done in a tablet press, such as in a steel die between two moving punches. When a solid composition comprises Compound I and another anti-HCV agent, it is possible to separately prepare solid dispersions of each individual active ingredient and then blend the optionally milled or ground solid dispersions before compacting. Compound I and another anti-HCV agent can also be prepared in the same solid dispersion, optionally milled and/or blended with other additives, and then compressed into tablets. Likewise, when a solid composition comprises Compound I and ritonavir, it is possible to separately prepare solid dispersions of each individual active ingredient and then blend the optionally milled or ground solid dispersions before compacting. Compound I and ritonavir can also be prepared in the same solid dispersion, optionally milled and/or blended with other additives, and then compressed into tablets.

At least one additive, such as one selected from flow regulators, lubricants, fillers, disintegrants or plasticizers, may be used in compressing the solid dispersion. These additives can be mixed with ground or milled solid dispersion before compacting. Disintegrants promote a rapid disintegration of the compact in the stomach and keeps the liberated granules separate from one another. Non-limiting examples of suitable disintegrants are cross-linked polymers such as cross-linked polyvinyl pyrrolidone, cross-linked sodium carboxymethylcellulose or sodium croscarmellose. Non-limiting examples of suitable fillers (also referred to as bulking agents) are lactose monohydrate, calcium hydrogenphosphate, microcrystalline cellulose (e.g., Avicell), silicates, in particular silicium dioxide, magnesium oxide, talc, potato or corn starch, isomalt, or polyvinyl alcohol. Non-limiting examples of suitable flow regulators include highly dispersed silica (e.g., colloidal silica such as Aerosil), and animal or vegetable fats or waxes. Non-limiting examples of suitable lubricants include polyethylene glycol (e.g., having a molecular weight of from 1000 to 6000), magnesium and calcium stearates, sodium stearyl fumarate, and the like.

Various other additives may also be used in preparing a solid composition prepared according to a process of the invention, for example dyes such as azo dyes, organic or inorganic pigments such as aluminium oxide or titanium dioxide, or dyes of natural origin; stabilizers such as antioxidants, light stabilizers, radical scavengers, stabilizers against microbial attack.

In one embodiment, a process of the invention described above uses Form A of Compound I which is substantially pure. Any Form A described above can be used in a process of the invention. For instance, the Form A crystal used can be at least 90% pure, preferably at least 95% pure, or more preferably at least 97%.

In another embodiment, a process of the invention described above uses Form B of Compound I which is substantially pure. Any Form B described above can be used in a process of the invention. For instance, the Form B crystal used can be at least 90% pure, preferably at least 95% pure, or more preferably at least 97%.

In another embodiment, a process of the invention described above uses Form C of Compound I which is substantially pure. Any Form C described above can be used in a process of the invention. For instance, the Form C crystal used can be at least 90% pure, preferably at least 95% pure, or more preferably at least 97%.

In another embodiment, a process of the invention described above uses Form D of Compound I which is substantially pure. Any Form D described above can be used in a process of the invention. For instance, the Form D crystal used can be at least 90% pure, preferably at least 95% pure, or more preferably at least 97%.

In another embodiment, a process of the invention described above uses Form E of Compound I which is substantially pure. Any Form E described above can be used in a process of the invention. For instance, the Form E crystal used can be at least 90% pure, preferably at least 95% pure, or more preferably at least 97%.

In another embodiment, a process of the invention described above uses Form F of Compound I which is substantially pure. Any Form F described above can be used in a process of the invention. For instance, the Form F crystal used can be at least 90% pure, preferably at least 95% pure, or more preferably at least 97%.

In another embodiment, a process of the invention described above uses Form G of Compound I which is substantially pure. Any Form G described above can be used in a process of the invention. For instance, the Form G crystal used can be at least 90% pure, preferably at least 95% pure, or more preferably at least 97%.

In another embodiment, a process of the invention described above uses Form H of Compound I which is substantially pure. Any Form H described above can be used in a process of the invention. For instance, the Form H crystal used can be at least 90% pure, preferably at least 95% pure, or more preferably at least 97%.

In another embodiment, a process of the invention described above uses Class 2 of Compound I which is substantially pure. Any Class 2 of Compound I described above can be used in a process of the invention. For instance, the Class 2 crystal used can be at least 90% pure, preferably at least 95% pure, or more preferably at least 97%.

In yet another aspect, the present invention features compositions comprising a crystalline form of Compound I of the invention. Any crystalline form described herein can be included in a composition of the invention. Preferably, the crystalline form is substantially pure, such as at least 90% pure, preferably at least 95% pure, or more preferably at least 97% pure. In one embodiment, a composition of the invention comprises at least 5% by weight of a substantially pure crystalline form of the invention. In another embodiment, the composition of the invention comprises at least 10% by weight of a substantially pure crystalline form of the invention. In still another embodiment, a composition of the invention comprises at least 5% by weight of one or more crystalline forms of the invention. In yet another embodiment, a composition of the invention comprises at least 10% by weight of one or more crystalline forms of the invention.

EXAMPLE 1

Preparation of Class 2 Crystalline Form of Compound I

A crystalline hydrate of Compound I prepared according to Example 49d of U.S. Patent Application Publication No. 2010/0144608 was added to a jacketed reactor at an internal temperature of 48° C., followed by a pre-mixed solvent mixture in volume fraction ratio of 0.2 isopropyl acetate, 0.4 isopropanol and 0.2 water. The resulting slurry was held at 48° C. for no less than 1 hour and then cooled to 10° C. and stirred for no less than 12 hours. Additional water was added to bring the solvent composition to volume fraction ratio of 0.2 isopropyl acetate, 0.4 isopropanol and 0.4 water. The slurry was drained, solids were filtered, then dried in vacuum oven at 32° C. and 5.3 in Hg for 60 minutes. Solids were analyzed by powder x-ray diffraction, and the diffraction pattern was found to conform to that of Class 2, which is a different crystalline form than the crystalline hydrate (herein "Class 1") described in Example 49d of U.S. Patent Application Publication No. 2010/0144608. A Class 2 crystalline form of Compound I can be produced with a significantly higher yield than Class 1 crystalline form.

EXAMPLE 2

Preparation of Crystalline Form D of Compound I 40 mg of crystalline Class 2 of Compound I was suspended in 1 ml of solvent mixture with a volume fraction composition of 0.2 isopropyl acetate, 0.4 isopropanol and 0.4 water. The solution was heated to 60° C. to produce a clear solution, and then cooled at a rate of 0.5° C./min to 20° C. with agitation. Crystals were isolated via vacuum filtration and used for single crystal structure determination. The structure was found to be Form D of Compound I, which contained 2.75 moles of water per mole of Compound I.

EXAMPLE 3

Preparation of Crystalline Form C of Compound I

Seed crystals of crystalline Class 2 of Compound I, with nominal size of 20 microns ($d_{50}$), were charged to solvent mixture with a volume fraction composition of 0.2 isopropyl acetate, 0.4 isopropanol and 0.4 water to create a seed bed. The seed bed was stirred at 40° C. A concentrated solution of Compound I was prepared in isopropyl acetate. A separate precipitating solvent mixture with a volume fraction composition of 0.5 isopropanol and 0.5 water was also prepared. The Compound I solution and the precipitating solvent mixture were simultaneously added to the seed bed while maintaining the temperature in the reactor at 40° C. and the overall volume fraction solvent composition in the reactor of 0.2 isopropyl acetate, 0.4 isopropanol and 0.4 water. Once all the Compound I solution and precipitating solvent mixture had been charged to the seed bed, the slurry was cooled to 20° C. and filtered using vacuum filtration. The solids were air dried on the filtration flask. One of the larger crystals was used for single crystal structure determination. The structure was found to be Form C of Compound I, which contained 2.5 moles of water per mole of Compound I.

EXAMPLE 4

Preparation of Crystalline Form A of Compound I

Form D of Compound I crystals were stored over desiccant for about 90 hours to produce crystalline Form A of Compound I.

EXAMPLE 5

Preparation of Crystalline Form B of Compound I

Form D of Compound I crystals were stored over desiccant for about 24 hours to produce crystalline Form B of Compound I.

EXAMPLE 6

Preparation of Class 2 Crystalline Form of Compound I

A ternary solvent mixture of the composition 0.2, 0.38 and 0.42 volume fractions isopropyl acetate, isopropyl alcohol and water was prepared. To an appropriate volume of the solvent a mixture of Class 1 and Class 2 crystals of Compound I were added to create an approximately 10 weight percent slurry. The slurry was stirred on a shaker block for six weeks. Intermittent dilutions were made to the slurry with the original solvent mixture to facilitate completion of crystal form conversion. The crystals were isolated via centrifugation, dried under ambient conditions overnight and analyzed for single crystal structure determination. The structure was found to be consistent with crystalline Class 2, which contained 2.25 moles of water per mole of Compound I.

EXAMPLE 7

Preparation of Class 2 Crystalline Form of Compound I

To a jacketed reactor at 40° C. a solvent mixture in volume fraction ratio of 0.21 isopropyl acetate, 0.39 isopropanol and 0.39 water was added. The solvent mixture was homogenized via an external rotor-stator device. A solution containing Compound I in isopropyl acetate at a concentration of 0.28 g/g and a pre-mixed binary solvent mixture in volume fraction ratio of 0.5 isopropanol and 0.5 water were prepared. The Compound I/isopropyl acetate solution was added directly to the homogenization device (tip speed 23 m/s), while the isopropyl alcohol/water mixture was added sub-surface into the jacketed reactor. The relative rates of addition of these two solutions were adjusted so that the final solvent composition in the jacketed reactor was maintained at volume fraction ratio of 0.21 isopropyl acetate, 0.39 isopropanol and 0.39 water during the entire charge. After the addition of an initial amount of the Compound I/isopropyl acetate solution along with the corresponding amount of isopropanol/water mixture, Class 2 crystalline seeds were added to the reactor. Another amount of the Compound I/isopropyl acetate solution along with the corresponding amount of isopropanol/water mixture was then added to further build the seed bed. At this point the internal temperature was increased to 55° C. and the homogenization device tip speed reduced to 5 m/s. The remaining Compound I/isopropyl acetate solution along with the corresponding amount of isopropanol/water mixture was added. Total addition time was approximately 3.5 hrs. At the completion of the simultaneous additions of the Compound I/isopropyl acetate and isopropanol/water solutions, more isopropanol water mixture was added to adjust the final solvent composition to a volume fraction ratio of 0.18 isopropyl acetate, 0.41 isopropanol and 0.41 water. The agitation was stopped and the slurry aged for 30 minutes. The slurry was cooled to 20° C. at rates ranging from 5-10° C./hr and then filtered. Wet solids were washed with 3 volumes of a ternary solvent mixture in volume fraction ratio of 0.21 isopropyl acetate, 0.39 isopropanol and 0.39 water. After air drying, the solids placed in an oven at 50° C. and 50% relative humidity. Solids were analyzed by powder x-ray diffraction and the diffraction pattern was found to conform to the Class 2 crystalline form. Particle size distribution of the crystalline solids isolated using this process was consistent among batches, as measured via Laser diffraction based wet method on Malvern Master-sizer.

The foregoing description of the present invention provides illustration and description, but is not intended to be exhaustive or to limit the invention to the precise one disclosed. Modifications and variations are possible in light of the above teachings or may be acquired from practice of the invention. Thus, it is noted that the scope of the invention is defined by the claims and their equivalents.

What is claimed is:

1. A crystalline form of Compound I:

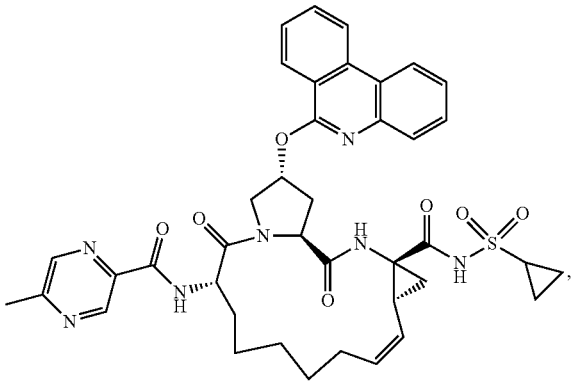

(I)

wherein, using a copper anode tube and a wavelength of 1.54178 Å, said crystalline form has characteristic peaks in PXRD pattern at values of two theta (° 2θ) of 10.7, 11.6, 12.7, 13.0, 13.2, 13.7, 14.5, 18.7, 19.0, and 19.9.

2. A crystalline form of Compound I:

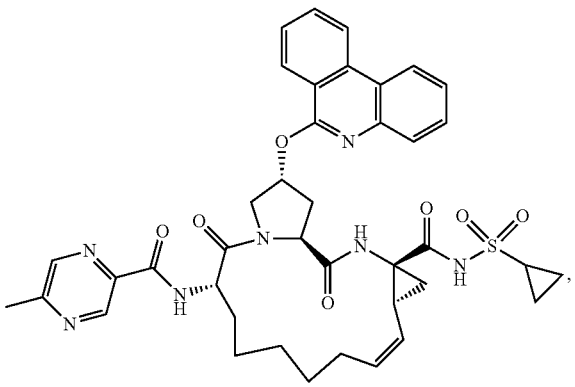

(I)

wherein, using a copper anode tube and a wavelength 1.54178 Å, said crystalline form has characteristic peaks in PXRD pattern at values of two theta (° 2θ) of 10.70, 11.57, 12.75, 13.02, 13.18, 13.66, 14.47, 18.66, 18.96, and 19.94.

3. The crystalline form of claim 1, wherein said crystalline form has characteristic peaks in PXRD pattern at values of two theta (° 2θ) of 10.5, 10.7, 11.6, 12.7, 13.0, 13.2, 13.7, 14.5, 17.3, 18.7, 19.0, 19.9, 21.9, 23.3, 24.3, 25.2, 25.6, 26.6, 27.2, and 30.0.

4. The crystalline form of claim 2, wherein said crystalline form has characteristic peaks in PXRD pattern at values of two theta (° 2θ) of 10.54, 10.70, 11.57, 12.75, 13.02, 13.18, 13.66, 14.47, 17.35, 18.66, 18.96, 19.94, 21.90, 23.31, 24.34, 25.19, 25.56, 26.64, 27.24, and 29.95.

5. The crystalline form of claim 1, wherein said crystalline form has characteristic peaks in PXRD pattern at values of two theta (° 2θ) of 5.8, 10.5, 10.7, 11.6, 12.7, 13.0, 13.2, 13.7, 14.5, 14.9, 17.3, 17.9, 18.7, 19.0, 19.7, 19.9, 20.5, 20.9, 21.4, 21.9, 22.4, 23.0, 23.3, 23.8, 24.3, 25.2, 25.6, 26.6, 27.2, and 30.0.

6. The crystalline form of claim 2, wherein said crystalline form has characteristic peaks in PXRD pattern at values of two theta (° 2θ) of 5.80, 10.54, 10.70, 11.57, 12.75, 13.02, 13.18, 13.66, 14.47, 14.88, 17.35, 17.92, 18.66, 18.96, 19.69, 19.94, 20.45, 20.86, 21.42, 21.90, 22.41, 22.98, 23.31, 23.84, 24.34, 25.19, 25.56, 26.64, 27.24, and 29.95.

7. The crystalline form of claim 1, wherein said crystalline form has characteristic PXRD peaks as shown in FIG. 7.

8. A composition comprising the crystalline form of claim 1.

9. A process for making a composition comprising Compound I, comprising dissolving the crystalline form of claim 1 in a solvent.

10. The process of claim 9, wherein said solvent is a hydrophilic polymer, and the crystalline form of claim 1 is dissolved in said polymer using melt extrusion.

11. A process for making the crystalline form of claim 1, comprising adding crystalline seeds of said crystalline form to a solution comprising Compound I.

12. The process of claim 11, wherein said seeds are produced from a supersaturated solution of Compound I using a homogenization device and in the presence of crystalline seeds of said crystalline form.

* * * * *